US009198639B2

(12) United States Patent
Frinking et al.

(10) Patent No.: US 9,198,639 B2

(45) Date of Patent: Dec. 1, 2015

(54) DETECTION OF IMMOBILIZED CONTRAST AGENT IN MEDICAL IMAGING APPLICATIONS BASED ON FLOW DYNAMICS ANALYSIS

(75) Inventors: Peter Frinking, Geneva (CH); Marcel Arditi, Geneva (CH); Nicolas Rognin, Geneva (CH); Feng Yan, Geneva (CH)

(73) Assignee: BRACCO SUISSE S.A., Manno (CH)

( * ) Notice: Subject to any disclaimer, the term of this patent is extended or adjusted under 35 U.S.C. 154(b) by 1789 days.

(21) Appl. No.: 12/084,933

(22) PCT Filed: Nov. 9, 2006

(86) PCT No.: PCT/EP2006/068305

§ 371 (c)(1), (2), (4) Date: May 12, 2008

(87) PCT Pub. No.: WO2007/054544

PCT Pub. Date: May 18, 2007

(65) Prior Publication Data

US 2009/0253986 A1 Oct. 8, 2009

(30) Foreign Application Priority Data

Nov. 10, 2005 (EP) .................................... 05110597

(51) Int. Cl.

*G06K 9/00* (2006.01)
*A61B 6/00* (2006.01)

(Continued)

(52) U.S. Cl.

CPC ............. *A61B 8/481* (2013.01); *G01S 7/52026* (2013.01); *G01S 7/52038* (2013.01); *G01S 7/52041* (2013.01); *G01S 7/52071* (2013.01); *G01S 7/52074* (2013.01); *A61B 8/08* (2013.01)

(58) Field of Classification Search

CPC . A61B 8/481; G01S 7/52026; G01S 7/52038; G01S 7/52041; G01S 7/52071; G01S 7/52074

USPC .......................... 600/458, 437; 382/128–133

See application file for complete search history.

(56) References Cited

U.S. PATENT DOCUMENTS 5,833,613 A * 11/1998 Averkiou et al. ............. 600/440
5,865,750 A 2/1999 Hatfield et al.

(Continued)

FOREIGN PATENT DOCUMENTS

EP 0374328 6/1990
EP A-0458745 A1 11/1991

(Continued)

OTHER PUBLICATIONS

PCT International Search Report for International Application No. PCT/EP2006/068305, European Patent Office, Feb. 16, 2007.

(Continued)

*Primary Examiner* — Long V Le
*Assistant Examiner* — Helene Bor
(74) *Attorney, Agent, or Firm* — Kevin D. Jablonski; Lane Powell PC

(57) ABSTRACT

A system for facilitating the detection of an immobilized contrast agent in medical imaging applications is proposed. The system includes means for providing a sequence of a total number of input images obtained at corresponding acquisition instants by imaging a body-part of a patient subjected to an administration of a contrast agent capable of circulating within the patient and of being substantially immobilized on a biological target, each input image including a plurality of input values each one indicative of a response to an interrogation signal of a corresponding portion of the body-part possibly including said contrast agent, and means for reducing a contribution of the circulating contrast agent within the body-part in at least one selected input image; the means for reducing includes means for creating a filtered image corresponding to each selected input image by replacing a set of input values of the selected input image with a set of corresponding filtered values, each filtered value being representative of the lowest response of the corresponding portion of the body-part in a set of multiple input images including the selected input image, the set of multiple input images consisting of a number of input images lower than the total number.

16 Claims, 14 Drawing Sheets

135 105 125 145 140 130 120 115 110 150 100 155

(51) Int. Cl.

| | |
|---|---|
| ***A61B 5/05*** | (2006.01) |
| ***A61B 8/08*** | (2006.01) |
| ***G01S 7/52*** | (2006.01) |

(56) References Cited

U.S. PATENT DOCUMENTS

| | | | |
|---|---|---|---|
| 6,436,049 B1 | 8/2002 | Kamiyama et al. | |
| 6,676,606 B2 * | 1/2004 | Simpson et al. | 600/458 |
| 2003/0097068 A1 | 5/2003 | Hossack et al. | |
| 2007/0126730 A1 | 6/2007 | Goto et al. | |

FOREIGN PATENT DOCUMENTS

| | | |
|---|---|---|
| EP | A-0554213 A1 | 8/1993 |
| EP | 1 568 323 A1 | 8/2005 |
| JP | 2003-164452 A | 10/2003 |
| JP | 2005-323657 A | 11/2005 |
| WO | WO-A-91/15244 | 10/1991 |
| WO | WO-A-94/09829 | 5/1994 |
| WO | WO 95/16467 | 6/1995 |
| WO | WO 2004/110279 A | 12/2004 |
| WO | 2005046478 | 5/2005 |
| WO | WO 2006/015971 A1 | 2/2006 |
| WO | WO 2006/018433 A1 | 2/2006 |
| WO | WO 2007/054544 A1 | 5/2007 |

OTHER PUBLICATIONS

Lindner, "Targeted Ultrasound Contrast Agents: Diagnostic and Therapeutic Potential", 2001 IEEE Ultrasonics Symposium, Oct. 7-10, 2001, pp. 1695-1703, vol. 2 of 2, New York, NY.

Weller et al., "Ultrasound Imaging of Acute Cardiac Transplant Rejection with Microbubbles Targeted to Intercellular Adhesion Molecule-1", Circulation, Jun. 30, 2003, pp. 218-224, vol. 108.

Lanza et al., "Targeted Ultrasonic Contrast Agents for Molecular Imaging and Therapy", Progress in Cardiovacular Diseases, Jul. 1, 2008, pp. 13-31, vol. 44, No. 1, Saunders, Philadelphia, PA.

Marsh et al., "Time-Evolution of Enhanced Ultrasonic Reflection Using a Fibrin-Targeted Nanoparticulate Contrast Agent", Ultrasonics Symposium, Oct. 22, 2000, pp. 1927-1930, vol. 2, Piscataway, NJ, USA.

Patrick Rafter, Patrick Phillips, Mani A. Vannan, "Imaging technologies and techniques" Cardiology Clinics 22 (2004), pp. 181-197.

Paul A. Dayton, David Pearson, Jarrod Clark, Scott Simon, Patricia Schumman, Reena Zutshi, Terry Matsunaga, Katherine W. Ferrara, "Ultrasonic Enhancement of αvβ3 Expressing-Cells With Targeted Contrast Agents", 2003 IEEE Ultrasonics Symposium, pp. 540-543.

* cited by examiner

DETECTION OF IMMOBILIZED CONTRAST AGENT IN MEDICAL IMAGING APPLICATIONS BASED ON FLOW DYNAMICS ANALYSIS

PRIORITY CLAIM

This application which claims priority from PCT/EP2006/068305, published in English, filed Nov. 9, 2006, based on European patent Application No. 05110597.1, filed Nov. 10, 2005, which are incorporated herein by reference.

TECHNICAL FIELD

An embodiment of the present invention relates to the medical imaging field. More specifically, an embodiment of the present invention relates to the detection of an immobilized contrast agent.

BACKGROUND

Medical imaging is a well-established technique (in the field of equipments for medical applications), which allows analyzing a body-part of a patient in a substantially non-invasive manner. A specific medical imaging technique is based on the recording of an echo signal that results from the application of ultrasound waves to the body-part. This technique may advantageously be implemented with the administration of an ultrasound contrast agent (UCA) to the patient (for example, consisting of a suspension of phospholipid-stabilized gas-filled microbubbles); as the contrast agent acts as an efficient ultrasound reflector, it enhances the visualization of a vascular system within the body-part where it is present.

Contrast agents, adapted to reach a specific (biological) target and then remain immobilized thereon, have also been proposed in the last years for facilitating the detection of specific pathologies. Particularly, these contrast agents are capable of attaching to selected tissues or receptors by means of a specific interaction therewith; for example, the desired behavior may be achieved by incorporating a targeting ligand in the formulation of the contrast agent (e.g., capable of interacting with tumoral tissues). In addition, contrast agents may also be conveyed or accumulated to a specific location, such as tissues or organs, by means of a non-specific interaction therewith; for example, the contrast agent may be recognized as a foreign substance by the immune system of the patient and then moved to the liver for its metabolism and elimination. In any case, once the contrast agent (either with specific or non-specific interaction) has reached the target remaining immobilized thereon, its detection may allow distinguishing pathologies that would be otherwise difficult to identify.

A possible problem associated with the detection of the immobilized contrast agent is that only a relatively small fraction of the total amount of the administered contrast agent actually reaches the target; conversely, most of the contrast agent continues to circulate (for example, until it is filtered out by the lungs and/or in the liver of the patient). The echo signal that is measured is then the result of different contributions, which are due to the immobilized contrast agent, to the circulating (free-flowing) contrast agent and to the surrounding tissues. Therefore, it may be quite difficult to distinguish the echo signal generated by the immobilized contrast agent from the one generated by the circulating contrast agent and the tissues; particularly, it may be almost impossible to differentiate the low concentration of immobilized contrast agent (often consisting of single particles thereof that reach the target individually) from the higher concentration of circulating contrast agent. This adversely affects the spatial delineation and the quantification of the immobilized contrast agent, thereby hindering the correct detection of the pathologies of interest.

Attempts have been made to improve the discrimination of the immobilized contrast agent. For example, "P. A. Dayton, D. Pearson, J. Clark, S. Simon, P. Schumann, R. Zutshi, T. Matsunaga, K. W. Ferrara, Ultrasonic Enhancement of $\alpha v\beta 3$ Expressing-Cells With Targeted Contrast Agents, 2003 IEEE Ultrasonics Symposium", which is incorporated by reference proposes a solution that is based on the observation that the echo signal corresponding to the immobilized contrast agent has a bandwidth that is narrower than the one of the circulating contrast agent. This document then mentions the possibility of discriminating the different contributions in the echo signal exploiting the larger bandwidth that is observed for the circulating contrast agent.

However, no solution is available in the art for detecting the immobilized contrast agent with an acceptable degree of accuracy. Particularly, the problem of efficiently discriminating the immobilized contrast agent from the circulating contrast agent is still unresolved. In this context, it would also be desirable to quantify the concentration of the immobilized contrast agent at each location.

Therefore, nowadays it may be necessary to wait until the circulating contrast agent has completely disappeared before being able to identify the immobilized contrast agent; however, this requires a relatively long time (up to tens of minutes).

All of the above hinders the clinical application of currently available contrast-specific imaging techniques for the detection of immobilized contrast agents.

SUMMARY

An embodiment of the present invention proposes a solution that exploits the difference in flow dynamics between the immobilized contrast agent and the circulating contrast agent.

Particularly, an embodiment of the invention proposes a system for facilitating the detection of an immobilized contrast agent in medical imaging applications. The system includes means (such as an ultrasound scanner) for providing a sequence of a total number of input images. The input images are obtained (at corresponding acquisition instants) by imaging a body-part of a patient subjected to an administration of a contrast agent (i.e., at least a portion of said images contains a signal generated by the contrast agent); the contrast agent is capable of being substantially immobilized (i.e., remaining in a substantially fixed position) on a biological target, being otherwise freely circulating within the patient's body (at least up to the time of its elimination from or metabolization by the body); for example, the contrast agent may attach selectively to specific tissues or receptors (by means of a specific interaction therewith) or it may be conveyed to or accumulated into specific tissues or organs (by means of a non-specific interaction therewith). Each input image includes a plurality of input values (i.e., pixel or voxel values); each input value is indicative of a response to an interrogation signal (such as an echo signal for ultrasound waves) of a corresponding portion of the body-part, which possibly includes said contrast agent. The system further includes means for reducing a contribution of the circulating contrast agent within the body-part in one or more selected input images. For this purpose, a filtered image corresponding to each selected input image is created. The result is achieved by replacing a set of input values of the selected input image (for example, in a desired region of interest) with a set of corresponding filtered values. Each filtered value is representative of the lowest response of the corresponding portion of the body-part in a set of multiple input images (including the selected input image); the set of multiple input images consists of a number of input images (two or more), which is lower than the total number.

In an embodiment of the invention, each filtered value consists of the minimum among the corresponding input values (in said set of multiple input images); for example, this result may be achieved by applying a modified version of the Minimum Intensity Projection (Min_IP) algorithm.

Typically, the set of multiple input images consists of the selected input image and at least one preceding input image in the sequence.

Two or more preceding input images are taken into account for this purpose.

According to an embodiment, the number of preceding input images is selected as a function of an estimated flow rate of the contrast agent (for example, increasing or decreasing it when the flow rate is low or high, respectively).

In a particular implementation, it is also possible to temporally sub-sample the preceding input images.

Typically, a contribution of the tissues in the input images has been already substantially removed, or at least reduced (for example, by acquiring them with a contrast-specific imaging mode).

A way to further improve the solution is of subtracting a background image (for example, taken before the arrival of the contrast agent in the body-part) from the input images.

In an implementation, the set of multiple input images is spatially sub-sampled according to an estimated resolution thereof (for example, based on the size of speckle grains that typically occur in ultrasound imaging).

As a further improvement, it is possible to compensate a relative motion of each input image (with respect to a selected reference image).

Moreover, the input images may also be linearized (so as to make their input values substantially proportional to a concentration of the contrast agent in the corresponding portions of the body-part).

An embodiment of the proposed solution is particularly advantageous when each filtered image is displayed substantially in real-time with the acquisition instants of the corresponding input image (i.e., with a short delay but without waiting for the completion of the analysis process).

The filtered images may be overlaid onto the corresponding selected input images.

Another embodiment of the present invention proposes a corresponding method.

A further embodiment of the present invention proposes a computer program for performing the method.

BRIEF DESCRIPTION OF THE DRAWINGS

Features and advantages of one or more embodiments will be best understood by reference to the following detailed description, given purely by way of a non-restrictive indication, to be read in conjunction with the accompanying drawings.

DETAILED DESCRIPTION

Figure 1:
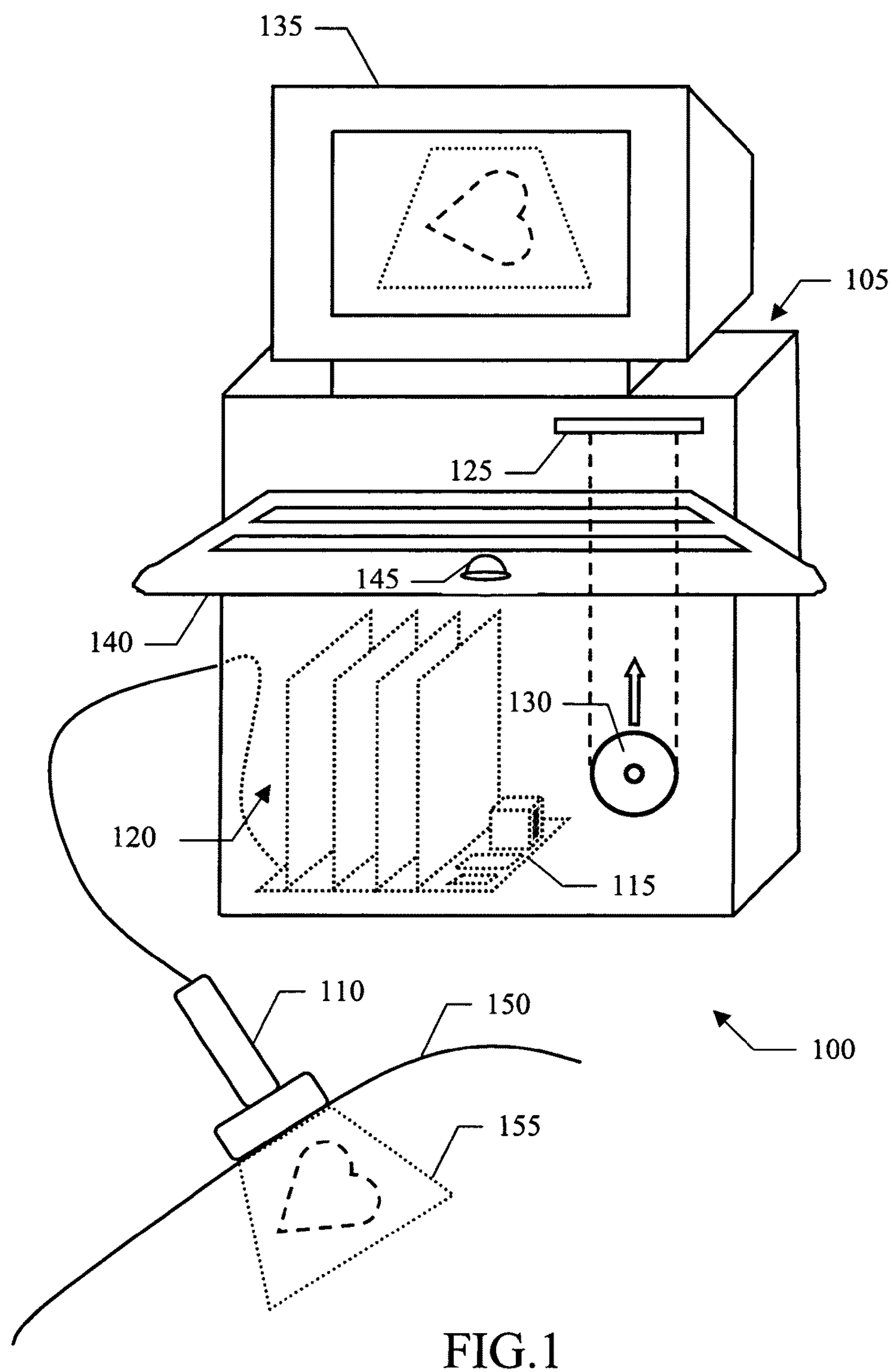
FIG. 1 is a pictorial representation of an ultrasound scanner in which the solution according to an embodiment of the invention is applicable.

FIG. 1 represents an example of a medical imaging system according to an embodiment of the invention. In particular, said imaging system is an ultrasound scanner 100, which includes a central unit 105 and a hand-held transmit-receive imaging probe 110 (for example, of the array type). The imaging probe 110 transmits ultrasound waves consisting of a sequence of insonifying ultrasound pulses (for example, having a center frequency between 2 and 10 MHz), and receives a (raw) radio-frequency (RF) echo signal resulting from the reflection of the ultrasound pulses; for this purpose, the imaging probe 110 is provided with a transmit/receive multiplexer, which allows using the imaging probe 110 in the pulse-echo mode.

The central unit 105 houses a motherboard 115, on which the electronic circuits controlling operation of the ultrasound scanner 100 (such as a microprocessor, a working memory and a hard-disk drive) are mounted. Moreover, one or more daughter boards (denoted as a whole with 120) are plugged on the motherboard 115; the daughter boards 120 provide the electronic circuits for driving the imaging probe 110 and for processing the received echo signal. The ultrasound scanner 100 may also be equipped with a drive 125 for reading removable disks 130 (such as floppy-disks). A monitor 135 displays images relating to the analysis in progress. Operation of the ultrasound scanner 100 is controlled by means of a keyboard 140, which is connected to the central unit 105 in a conventional manner; preferably, the keyboard is provided with a trackball 145 that is used to manipulate the position of a pointer (not shown in the FIG.) on a screen of the monitor 135.

In ultrasound imaging applications, the imaging probe 110 is typically placed in contact with the skin of a patient 150 in the area of a body-part 155 to be analyzed.

In general, a contrast agent capable of being immobilized on a selected target is administered to the patient, so that the body-part under analysis receives said contrast agent. Depending on the chosen imaging technique, the contrast agent can be specific for enhancing, for instance, Ultrasound images, Magnetic Resonance images or X-ray Computed Tomography images. The contrast agent can be administered orally (for example, for imaging the gastro-intestinal tract), via nebulizer into the airways (for imaging the lungs), or by injection. Administration by injection includes, for instance, intravascular (such as intravenous or intra-arterial), intralymphatic, subcutaneous, intramuscular, intradermal, intraperitoneal, interstitial, intrathecal or intratumoral administration. The contrast agent may be administered by injection, intravenously, either as a continuous infusion (typically by means of a pump) or as a bolus (typically by hand with a syringe), so that the body-part under analysis is perfused with said contrast agent. Depending on the different imaging techniques, the contrast agent may be administered to the patient before and/or during the acquisition of the images of the body-part.

The contrast agent is substantially free to circulate within the patient, so as to be received by the body-part under analysis; for example, the contrast agent can move along the gastrointestinal tract (in case of oral administration), or within the vascular system (in case of intravascular administration). However, the contrast agent is also capable of being immobilized on a selected (biological) target, so as to remain in a substantially fixed position for the whole duration of the analysis process (or at least a large portion thereof).

The contrast agent is capable of enhancing ultrasound images, such as the images acquired with the system of FIG. 1.

Suitable contrast agents for ultrasound imaging include suspensions of gas bubbles in a liquid carrier; typically, the gas bubbles have diameters on the order of 0.1-5 μm, so as to allow them to pass through the capillaries of the body of the patient. The gas bubbles are generally stabilized by entraining or encapsulating the gas or a precursor thereof into a variety of systems, including emulsifiers, oils, thickeners, sugars, proteins or polymers; stabilized gas bubbles are referred to as gas-filled microvesicles. The microvesicles include gas bubbles dispersed in an aqueous medium and bound at the gas/liquid interface by a very thin envelope involving a surfactant, i.e., an amphiphilic material (also known as microbubbles). Alternatively, the microvesicles include suspensions in which the gas bubbles are surrounded by a solid material envelope formed of lipids or of natural or synthetic polymers (also known as microballoons or microcapsules). Another kind of contrast agent includes suspensions of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial ultrasound contrast agent comprising gas-filled microvesicles is SonoVue® by Bracco International BV.

The contrast agent may be formulated in such a way as to selectively bind to a desired target by means of a specific interaction therewith; in this case, it is commonly referred to as a targeted contrast agent. For example, this behavior can be achieved by incorporating a targeting ligand capable of selectively binding (such as through biochemical affinity and/or electrostatic interaction) to a desired tissue or receptor. Examples of targeting ligands (which may be inserted into a membrane of the microbubbles) are monoclonal antibodies, peptides, or polysaccharides. The term tissue includes within its meaning individual cells as well as aggregates of cells, such as membranes or organs. The term refers to either normal (healthy) or abnormal (pathological) cells or aggregates of cells. Examples of tissues are myocardial tissues (including myocardial cells and cardiomyocites), membranous tissues (such as endothelium and epithelium), and connective tissues; examples of pathological tissues are infarcted heart tissues, blood clots, atherosclerotic plaques and tumoral tissues. The receptors include any molecular structure located on the tissues (for example, within the cells or on their surfaces), which is capable to selectively bind to a specific substance. Exemplary receptors are glycoprotein GPIIbIIIa or fibrin (for example, located in blood clots or thrombi) or KDR (for example, located in tumoral tissues). Examples of suitable targeted contrast agents and of targeting ligands are described in "G. M. Lanza and S. A. Wickline, Targeted Ultrasonic Contrast Agents for Molecular Imaging and Therapy, Progress in Cardiovascular Diseases, 44(1), 2001, 13-31", and in the co-pending International Patent Application No. PCT/EP2005/054041 filed on 17 Aug. 2005 (the entire disclosures of which are herein incorporated by reference).

Also contrast agents without specific targeting ligands may nevertheless be immobilized at specific locations of the patients by means of non-specific interactions therewith. For example, depending on their formulation and size, certain gas-filled microvesicles may be rapidly recognized as non-self components of the blood, thus being opsonized by blood proteins and then phagocytosed by monocytes or macrophages. In this case, generally, a large fraction of the gas-filled microvesicles ends up in the liver. Alternatively, gas-filled microvesicles (which are less rapidly recognized as non-self components of the blood) may extend their circulation time up to at least 20 minutes. For these gas-filled microvesicles a slow accumulation thereof can occur in certain organs (for example, the kidney); therefore, at late times after administration the gas-filled microvesicles can be slowly moving or completely stopped in these organs. The quantification of the above-described phenomenon, also known in the art as Late Phase Opacification (LPO), may provide valuable information about the status of the organs at issue.

With reference again to FIG. 1, a series of ultrasound pulses with low acoustic energy (such as with a mechanical index MI=0.01-0.1) is applied to the body-part 155, so as to involve a negligible destruction of the contrast agent (such as less than 20%, and for example less than 10% of its total amount). The echo signal that is recorded in response to the ultrasound pulses over time provides a representation of the evolution of the body-part 155 during the analysis process (either while the patient 150 undergoing the administration of the contrast agent or later on). The echo signal is then converted into a sequence of digital images (or frames) in standard Brightness mode (B-mode), which images represent the body-part 155 at corresponding successive acquisition instants (for example, with a sampling rate of 10-30 images per second). Each image is defined by a bitmap consisting of a matrix (for example, with 512 rows and 512 columns) of values for respective visualizing elements, i.e., basic picture elements (pixels) or basic volume elements (voxels), each one corresponding to a location consisting of a basic portion of the body-part 155. Typically, the pixel value consists of a gray-scale level (for example, coded on 8 bits) defining the brightness of the pixel; the pixel value increases from 0 (black) to 255 (white) as a function of the intensity of the corresponding echo signal.

The echo signal and then the corresponding images generally result from the superimposition of different contributions, which are generated by the contrast agent that is still circulating, the contrast agent that is immobilized on the target, and the surrounding tissues. The ultrasound scanner 100 may operate in a contrast-specific imaging mode so as to substantially remove, or at least reduce, the dominant (linear) contribution of the tissues in the echo signal, with respect to the (non-linear) contribution of the (circulating and immobilized) contrast agent; examples of contrast-specific imaging modes include harmonic imaging (HI), pulse inversion (PI), power modulation (PM) and contrast pulse sequencing (CPS) techniques, as described, for example, in "Rafter et al., Imaging technologies and techniques, Cardiology Clinics 22 (2004), pp. 181-197" (the entire disclosure of which is herewith incorporated by reference).

In order to allow discriminating the immobilized contrast agent from the circulating contrast agent, an embodiment of a solution described in the following starts from the observation that the contribution of the immobilized contrast agent shows a high level of correlation over time, in contrast to the contribution of the circulating contrast agent that instead shows a low level of correlation. The highly correlated echo signal is represented in the sequence of images by corresponding pixel values (for the same location) that exhibit small or no variation (from one instant to the other); conversely, the echo signal with low correlation is represented by corresponding pixel values that exhibit a high variation. The images are then processed so as to substantially suppress (or at least attenuate) the pixel values showing high variations (at the same time preserving the pixel values showing low variations).

For this purpose, each pixel value is replaced by the minimum between the pixel value itself and the corresponding pixel value in the preceding image. More formally, the pixel value is obtained by applying the following proposed algorithm:

$$OP(x,y,k)=\mathrm{MIN}[IP(x,y,k),IP(x,y,k-1)],$$

where OP(x,y,k) is the (output) processed value of the pixel identified by the spatial coordinates x,y (numbers of row and column, respectively) in the image taken at the instant k, IP(x,y,k) and IP(x,y,k−1) are the (input) original values of the pixel in the same image and in the preceding one, and MIN[ ] is a function determining the minimum between its arguments.

Figures 2A, 2B:
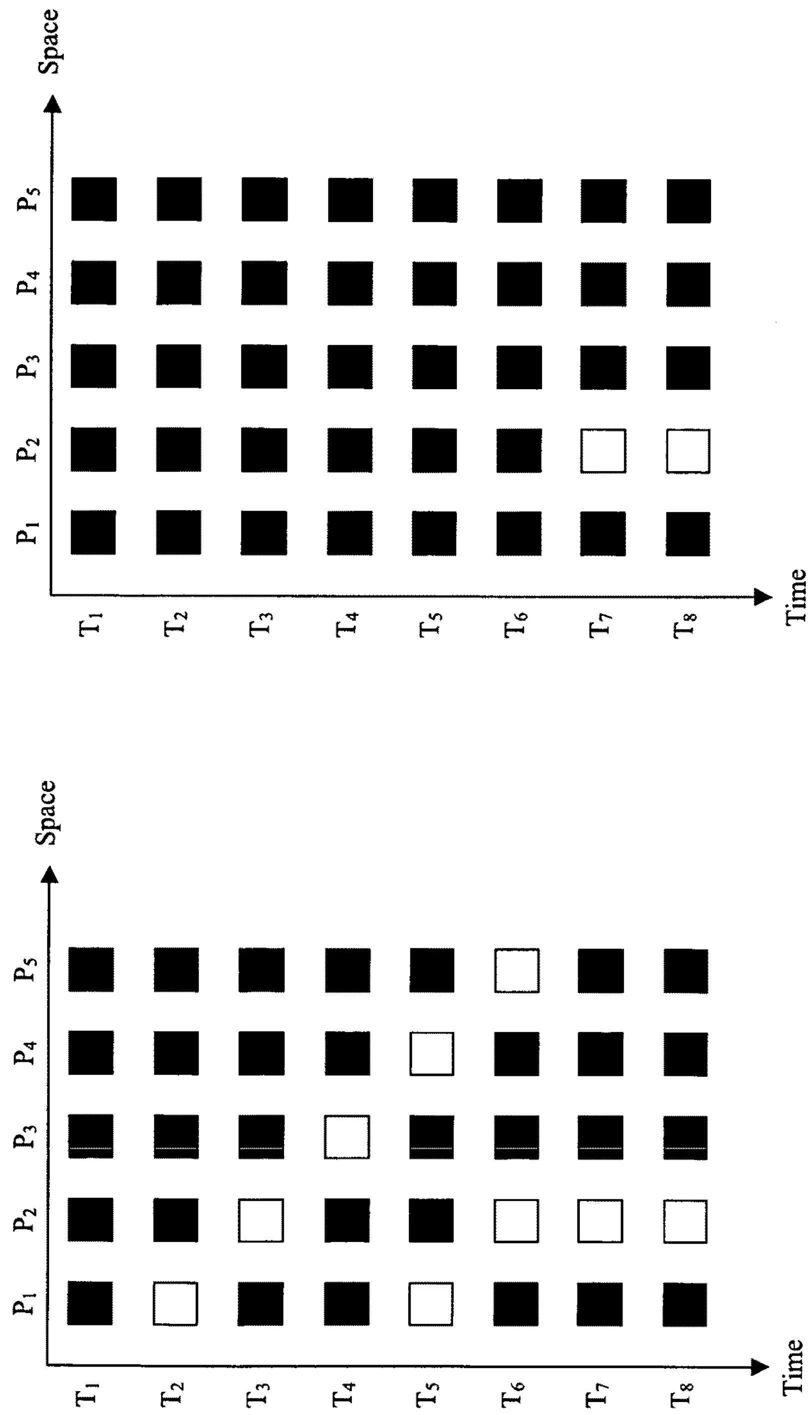
FIGS. 2*a*-2*b* are a schematic representation of an exemplary application of the solution according to an embodiment of the invention.

An example of application of the above-mentioned algorithm is represented schematically in FIGS. 2*a*-2*b*. Particularly, FIG. 2*a* shows a portion (consisting of 5 pixels $P_1$-$P_5$) of exemplary images taken at consecutive instants ($T_1$-$T_8$). For the sake of simplicity, each pixel $P_1$-$P_5$ is represented as completely black in the absence of contrast agent and completely white when the contrast agent is detected.

As shown in the FIG., at the beginning (instant $T_1$) all the pixels $P_1$-$P_5$ are black to indicate that no contrast agent is present in the corresponding region of the body-part (assuming that the contribution in the echo signal due to the tissues has been completely suppressed). A first particle of contrast agent (such as a microbubble) enters the same region at the instant $T_2$, as shown by the pixel $P_1$ that becomes white. The first particle of contrast agent then crosses the region from the left to the right (white pixels $P_2$-$P_5$ at the instants $T_3$-$T_6$), and leaves it at the instant $T_7$. In addition to the first particle, a second particle of contrast agent enters the region (white pixel $P_1$) at the instant $T_5$. The second particle of contrast agent moves to the next pixel $P_2$ at the instant $T_6$, and then remains immobilized at this position (instants $T_6$-$T_8$).

The application of the proposed algorithm to the example described above generates a corresponding image that is shown in FIG. 2*b*. Particularly, every pixel $P_1$-$P_5$ that changes between consecutive images becomes black (since it is replaced by the corresponding minimum calculated by the algorithm); conversely, when a pixel $P_1$-$P_5$ is stationary (between consecutive images) it remains at its value. As a result, the contribution of the first (circulating) particle of contrast agent disappears; the second particle of contrast agent is not shown when it is moving (instants $T_5$-$T_6$), but it is detected as soon as it is immobilized (instants $T_7$-$T_8$).

Naturally, in a real application each pixel can be represented by any gray-scale level. Particularly, the pixel values are a function of the concentration of contrast agent; the pixels are quite dark in the presence of low concentrations of contrast agent (such as when few particles thereof are immobilized) while they are very bright in the presence of high concentrations of contrast agent (such as when the circulating contrast agent enters the body-part under analysis during the wash-in phase).

Figures 3A, 3B:
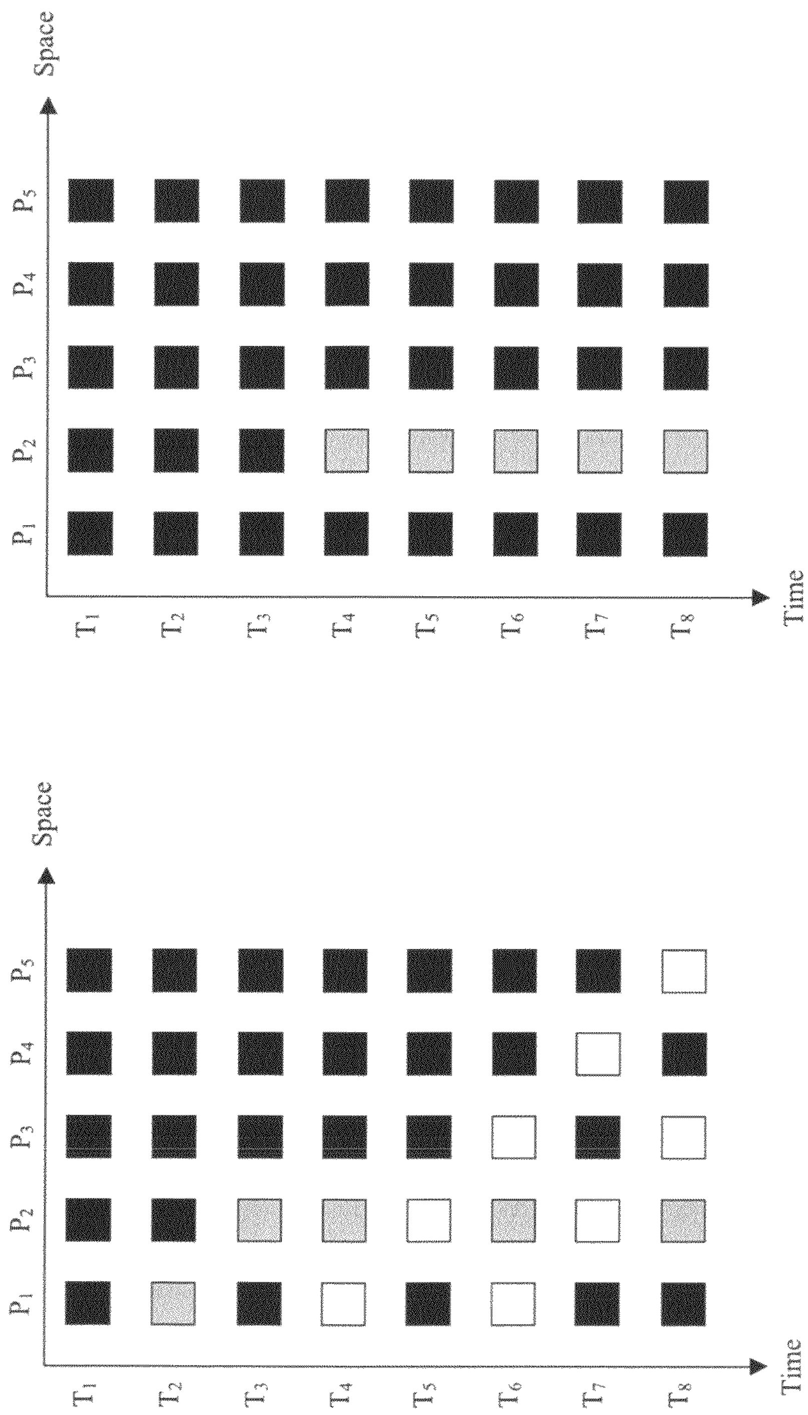
FIGS. 3*a*-3*b* are a schematic representation of a different exemplary application of the solution according to the same embodiment of the invention.

For example, as shown in FIG. 3*a*, at the beginning (instant $T_1$) all the pixels $P_1$-$P_5$ are black (no contrast agent). A particle of contrast agent enters the region at the instant $T_2$ (as shown by the pixel $P_1$ that becomes gray); the particle of contrast agent moves to the next pixel $P_2$ at the instant $T_3$, and then remains immobilized in this position (instants $T_4$-$T_8$). In the representation of FIG. 3*a*, further circulating particles of contrast agent cross the region from the left to the right at the instants $T_4$-$T_8$ (white pixels $P_1$-$P_5$) and at the instants $T_6$-$T_8$ (white pixels $P_1$-$P_3$). As can be seen, the contribution of the circulating contrast agent is predominant, and substantially hides the presence of the immobilized contrast agent.

The application of the proposed algorithm to this example generates a corresponding image that is shown in FIG. 3*b*. In this case as well, the contribution of the circulating contrast agent disappears leaving only the contribution of the immobilized contrast agent (gray pixel $P_2$ at the instants $T_4$-$T_8$).

Figure 4A:
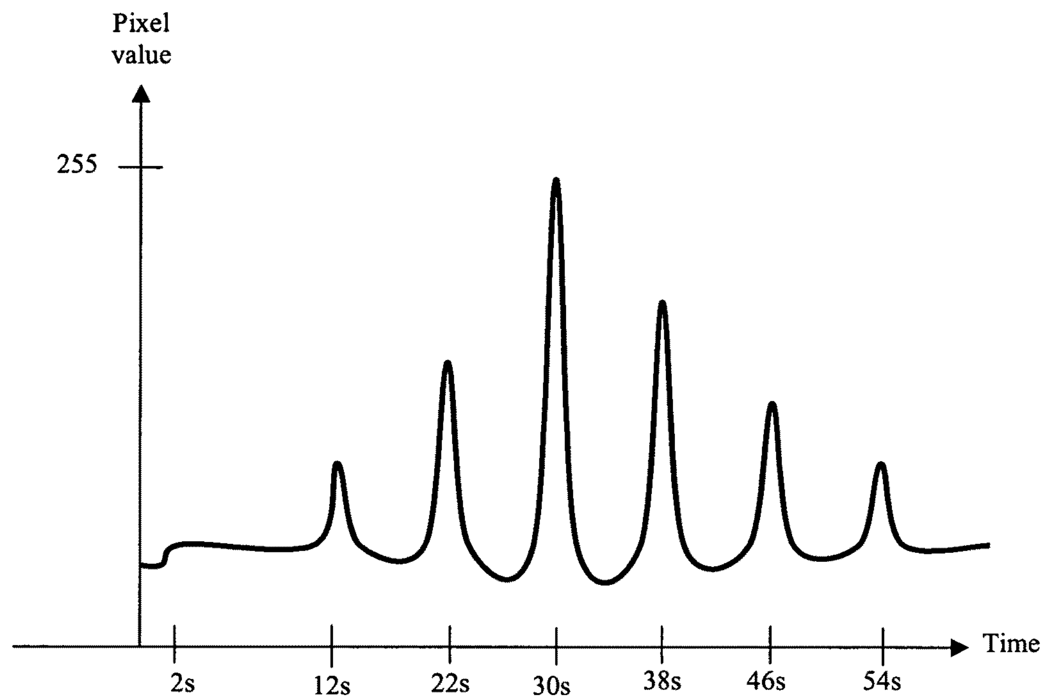
FIGS. 4*a*-4*b* are time diagrams explaining operation of the solution according to an embodiment of the invention.

In other words, the above-described processing filters out the (high-intensity) peaks of the pixel values over time. In order to explain this behavior, an exemplary sequence of corresponding pixel values for the same location is shown in FIG. 4*a*. As can be seen, a particle of contrast agent is immobilized in the pixel location at the instant about 2 s (as indicated by the slight increase of the pixel value). A large number of circulating particles of contrast agent then crosses the same pixel at the instants about 12 s, 22 s, 30 s 38 s, 46 s, and 54 s (as indicated by the far higher increases of the pixel value).

Figure 4B:
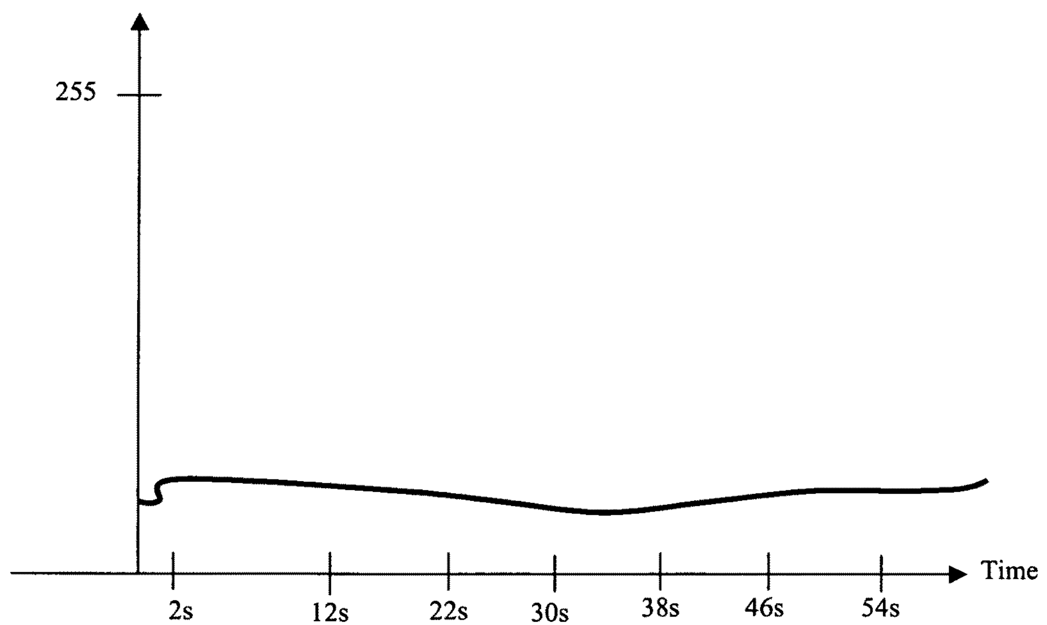

However, as shown in FIG. 4*b*, the application of the proposed algorithm results in a pattern of the pixel values that is substantially flat (after the detection of the immobilized particle of contrast agent). Indeed, the peaks caused by the passage of the circulating particles of contrast agent are very short, so that the algorithm will always compare the corresponding high pixel value with the preceding low pixel value due to the immobilized particle of contrast agent; in this way, those peaks disappear leaving the contribution of the immobilized particle of contrast agent only.

The proposed algorithm is derived from the Minimum Intensity Projection (Min_IP) algorithm, and it will be referred to as "modified Min_IP algorithm" hereinafter. In the (original) Min_IP algorithm, each pixel value is replaced with the minimum between the pixel value itself and the running minimum resulting from the earlier iterations of the process, that is:

$$OP(x,y,k)=\mathrm{MIN}[IP(x,y,k),OP(x,y,k-1)],$$

where OP(x,y,k−1) is the (output) processed value of the pixel in the preceding image.

However, it should be noted that with the Min_IP algorithm it may be impossible to detect the immobilized contrast agent.

Figure 5B:
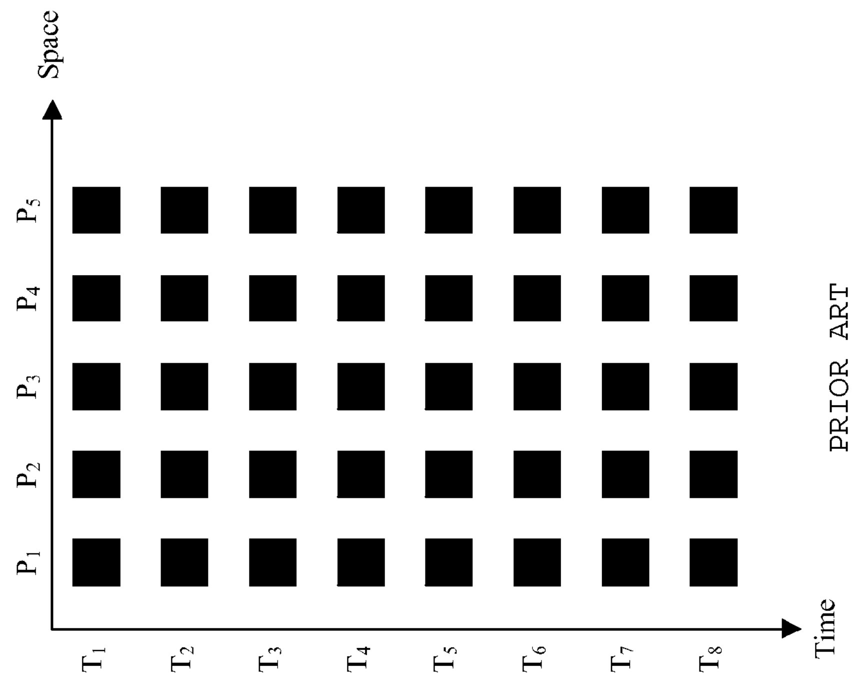
FIGS. 5*a*-5*b* are a schematic representation of the application of the minimum intensity projection algorithm known in the art.
Figure 5A:
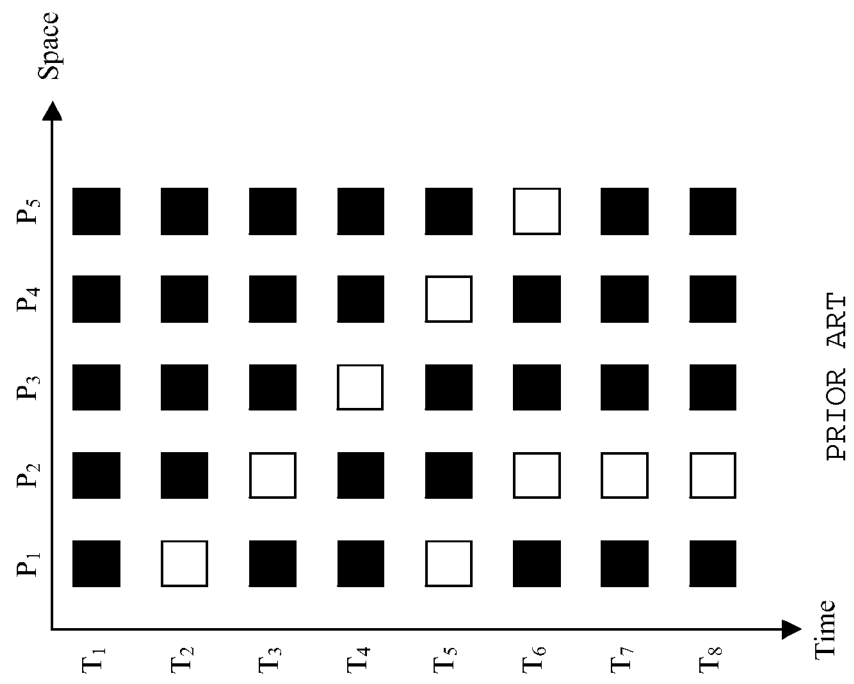

For example, in FIG. 5*a* the same scenario provided in FIG. 2*a* is taken into consideration.

The application of the Min_IP algorithm to this example generates a corresponding image that is shown in FIG. 5*b*. Particularly, every pixel $P_1$-$P_5$ that has become black always maintains the same value (since the Min_IP algorithm replaces it with its running minimum). Therefore, when a particle of contrast agent is immobilized, the corresponding pixel ($P_2$) is not updated and remains black.

Similar considerations apply to the Maximum Intensity Projection (Max_IP) algorithm. In the Max_IP algorithm, each pixel value is replaced with the maximum between the pixel value itself and the running maximum resulting from the earlier iterations of the process, that is:

$$OP(x,y,k)=\mathrm{MAX}[IP(x,y,k),OP(x,y,k-1)],$$

where MAX[ ] is a function determining the maximum between its arguments.

However, even with the Max_IP algorithm it may be impossible to detect the immobilized contrast agent. For example, in FIG. 6*a* the same scenario provided in FIG. 2*a* is taken into consideration again.

Figure 6B:
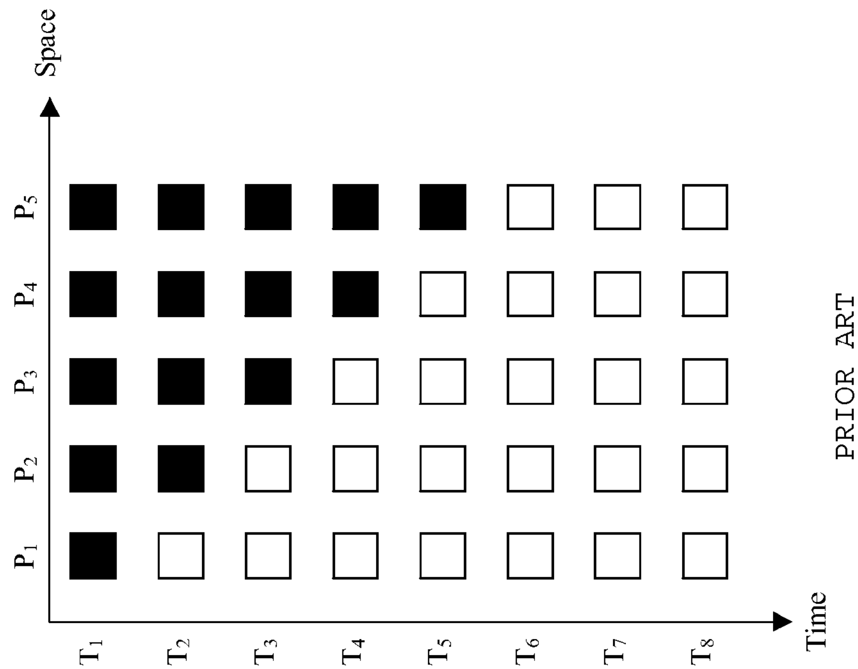
FIGS. 6*a*-6*b* are a schematic representation of the application of the maximum intensity projection algorithm known in the art.
Figure 6A:
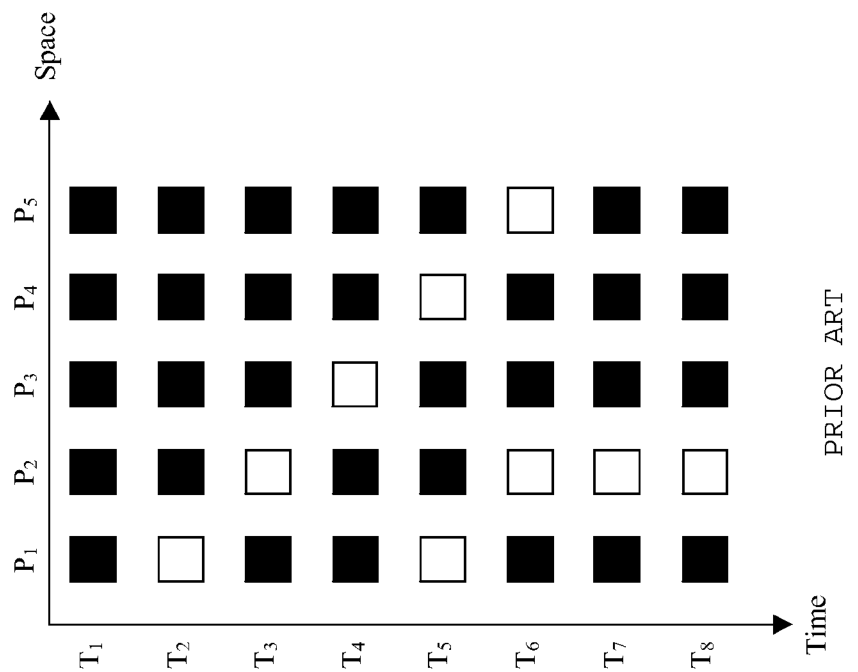

The application of the Max_IP algorithm to this example generates a corresponding image that is shown in FIG. 6*b*. Particularly, every pixel $P_1$-$P_5$ that has become white always maintains the same value (since the Max_IP algorithm replaces it with its running maximum). Therefore, once the circulating contrast agent reaches a generic pixel $P_1$-$P_5$, this pixel remains white even when the circulating contrast agent has left it. As a result, the circulating contrast agent completely masks the immobilized contrast agent (at the pixel $P_2$).

The Min_IP and the Max_IP algorithms are used in the medical imaging field, for example, to improve the visualization of the vascular system (e.g., by applying the Min_IP algorithm before the administration of the contrast agent and subsequently applying the Max_IP algorithm after the administration of the contrast agent); particularly, this technique is described for the production of (three-dimensional) projection images in U.S. Pat. No. 6,436,049, which is incorporated by reference. Another application of the Max_IP algorithm is disclosed in U.S. Pat. No. 6,676,606, which is incorporated by reference; in this case, the Max_IP algorithm is used to project the trajectories of the particles of contrast agent, so as to allow detecting tiny blood vessels (especially useful when they are crossed by individual particles of contrast agent).

Referring back to the modified Min_IP algorithm, it has been observed that (although quite effective in discriminating the immobilized contrast agent in many practical applications) this algorithm might show some limitations in specific critical conditions (e.g., when a high concentration of circulating particles of contrast agent is present or when the circulating particles of contrast agent move slowly).

Figure 7B:
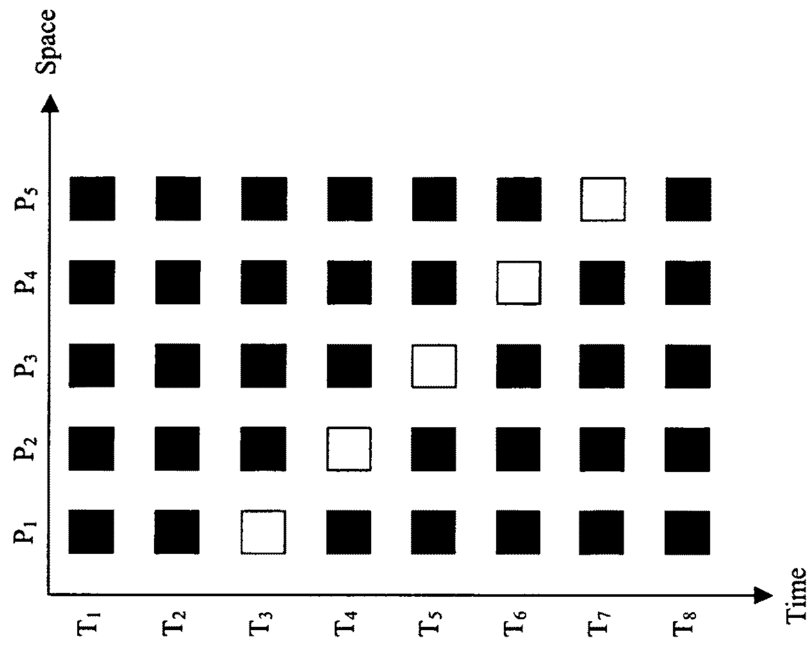
FIGS. 7*a*-7*b* are a schematic representation of an exemplary application of a solution according to an embodiment of the invention in a critical condition.
Figure 7A:
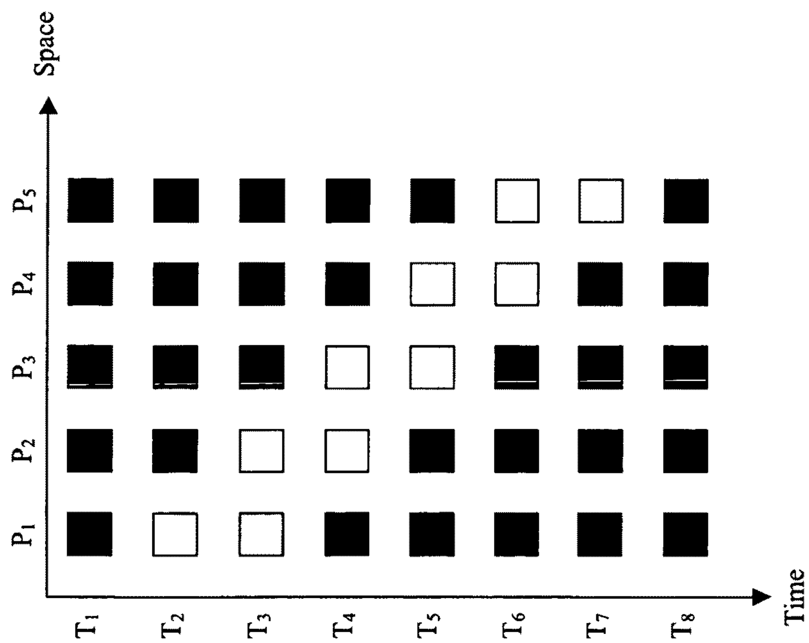

For example, the application of the modified Min_IP algorithm to an exemplary condition with a high concentration of circulating particles of contrast agent is represented schematically in FIGS. 7*a*-7*b*.

Particularly, as shown in FIG. 7*a*, at the beginning (instant $T_1$) all the pixels $P_1$-$P_5$ are black (no contrast agent). A first circulating particle of contrast agent crosses the region from the left to the right (white pixels $P_1$-$P_5$ at the instants $T_2$-$T_6$); the first circulating particle of contrast agent is directly followed by a second circulating particle of contrast agent that crosses the same region from the left to the right immediately afterwards (white pixels $P_1$-$P_5$ at the instants $T_3$-$T_7$).

The application of the modified Min_IP algorithm to the example described above generates a corresponding image that is shown in FIG. 7*b*. As in the preceding case, the contribution of the first circulating particle of contrast agent disappears. However, this is not true for the second circulating particle of contrast agent (since every pixel $P_1$-$P_5$ remains white for two consecutive instants as the circulating particles of contrast agent cross it in succession); therefore, the contribution due to the second circulating particle of contrast agent remains visible in the image even after the application of the modified Min_IP algorithm, with the risk of hindering the detection of any actually immobilized particle of contrast agent in the same region.

Figure 8B:
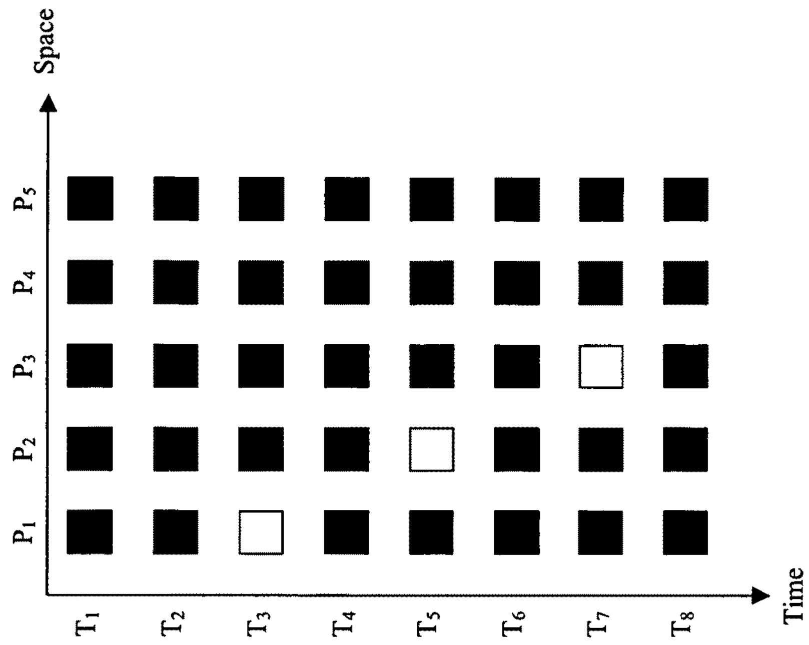
FIGS. 8*a*-8*b* are a schematic representation of an exemplary application of a solution according to an embodiment of the invention in another critical condition.
Figure 8A:
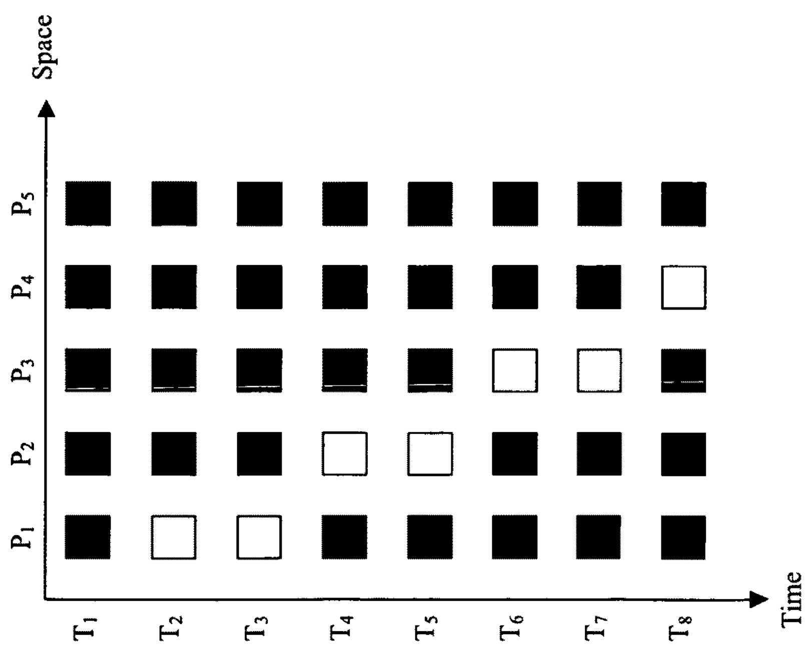

Likewise, the application of the modified Min_IP algorithm to an exemplary condition with slowly moving circulating particles of contrast agent is represented schematically in FIGS. 8*a*-8*b*.

Particularly, as shown in FIG. 8*a*, at the beginning (instant $T_1$) all the pixels $P_1$-$P_5$ are black (no contrast agent). A slowly moving circulating particle of contrast agent enters the region at the instant $T_2$, as shown by the pixel $P_1$ that becomes white; the slowly moving circulating particle of contrast agent is again in the same position at the next instant $T_3$. The slowly moving circulating particle of contrast agent then moves to the pixel $P_2$ (instants $T_4$-$T_5$), to the pixel $P_3$ (instants $T_6$-$T_7$), and to the pixel $P_4$ (instant $T_8$).

The application of the modified Min_IP algorithm to the example described above generates a corresponding image that is shown in FIG. 8*b*. As can be seen, whenever a pixel remains stationary (i.e., the pixel $P_1$ at the instants $T_2$-$T_3$, the pixel $P_2$ at the instants $T_4$-$T_5$, and the pixel $P_3$ at the instants $T_6$-$T_7$) it becomes white (at the instants $T_3$, $T_5$ and $T_7$, respectively). Therefore, the slowly moving circulating particle of contrast agent is seen as immobilized at these instants (thereby introducing an artifact in the resulting image).

In other words, the modified Min_IP algorithm (in the form provided above) is unable to discriminate the immobilized particles of contrast agent from the circulating particles of contrast agent that remain around the same pixel location for a period longer than the time interval between two consecutive images (because they either are close to each other or move slowly). Indeed, the peaks caused by the passage of the circulating particles of contrast agent that are too broad cannot be removed (since they have exactly the same behavior as the immobilized particles of contrast agent).

However, the above-mentioned problem may be solved by increasing the filtering length of the modified Min_IP algorithm (defined by the number of images that are taken into consideration for calculating the minimum). For example, with a filtering length of 3 images, the formula defining the modified Min_IP algorithm becomes:

$$OP(x,y,k)=\mathrm{MIN}[IP(x,y,k),IP(x,y,k-1),IP(x,y,k-2)],$$

where IP(x,y,k−2) is the (input) original value of the pixel in the next preceding image. In this way, any particle of contrast agent will be considered immobilized only when it remains in the same location for three or more consecutive images; therefore, this allows filtering out peaks of the pixel values that are broader.

Figure 9B:
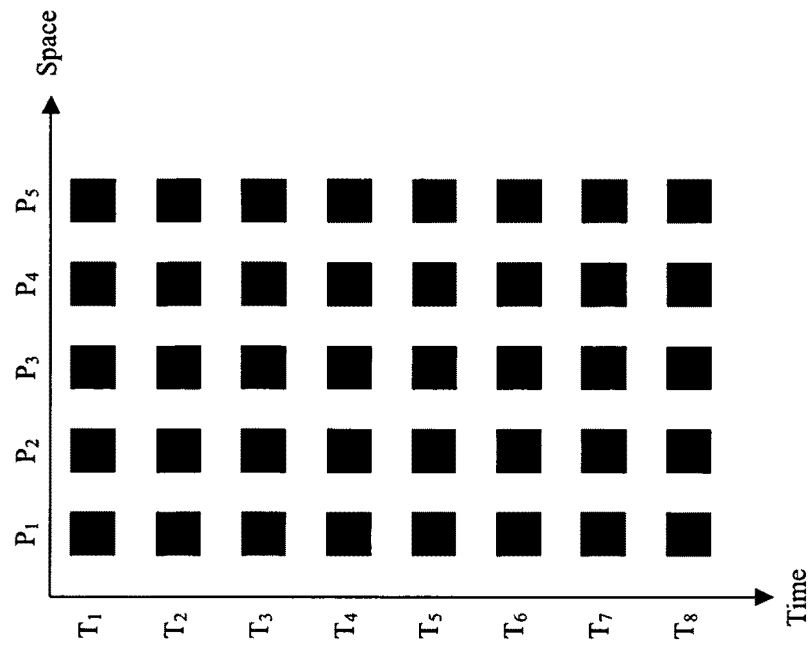
FIGS. 9*a*-9*b* are a schematic representation of an exemplary application of a solution according to a further embodiment of the invention.
Figure 9A:
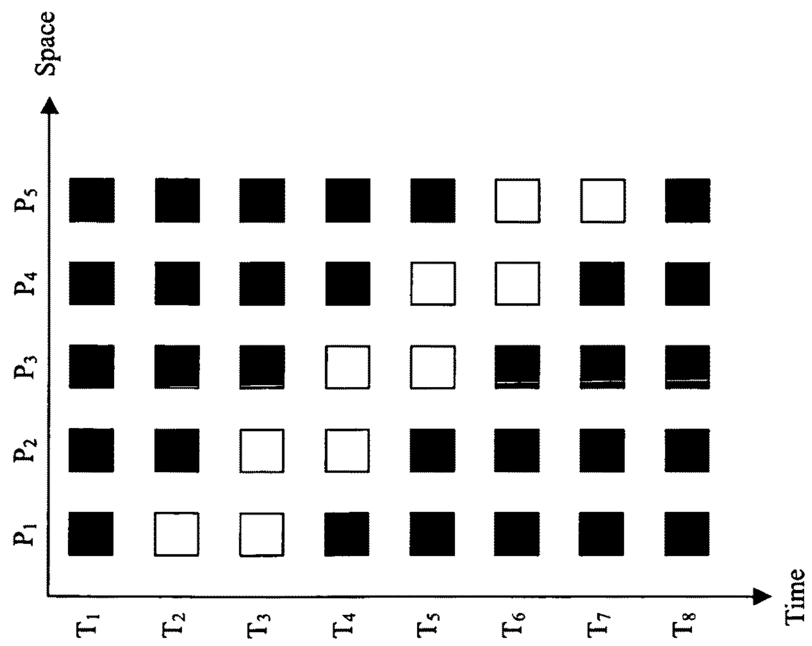

In order to explain this behavior, in FIG. 9*a* the same scenario provided in FIG. 7*a* is taken into consideration.

The application of the modified Min_IP algorithm with a filtering length of 3 images to this example generates a corresponding image that is shown in FIG. 9*b*. As can be seen, every pixel $P_1$-$P_5$ is black (since the algorithm replaces it with its minimum over the last three images). Therefore, the contribution of all the circulating particles of contrast agent now disappears (even if they cross the same pixel location at two consecutive instants).

Figure 10B:
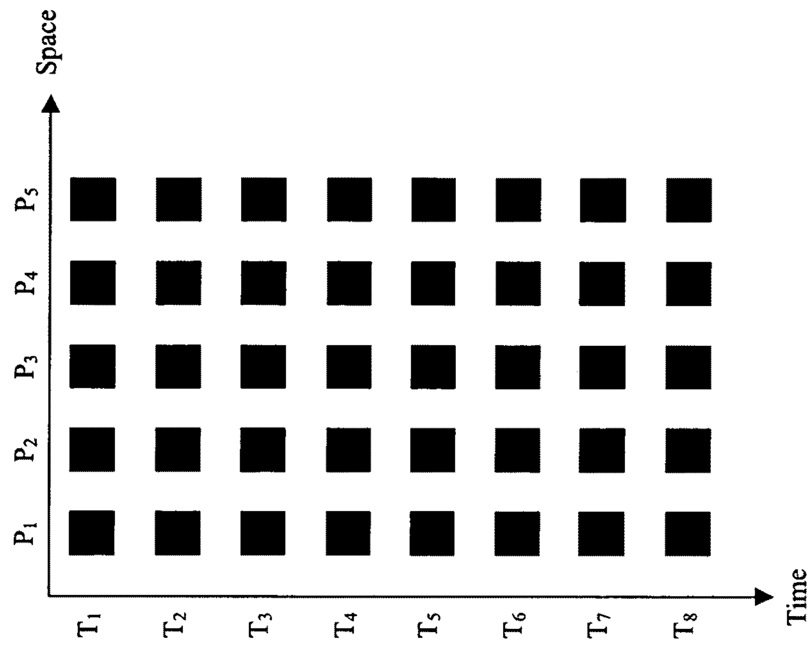
FIGS. 10*a*-10*b* are a schematic representation of a different exemplary application of a solution according to the same embodiment of the invention.
Figure 10A:
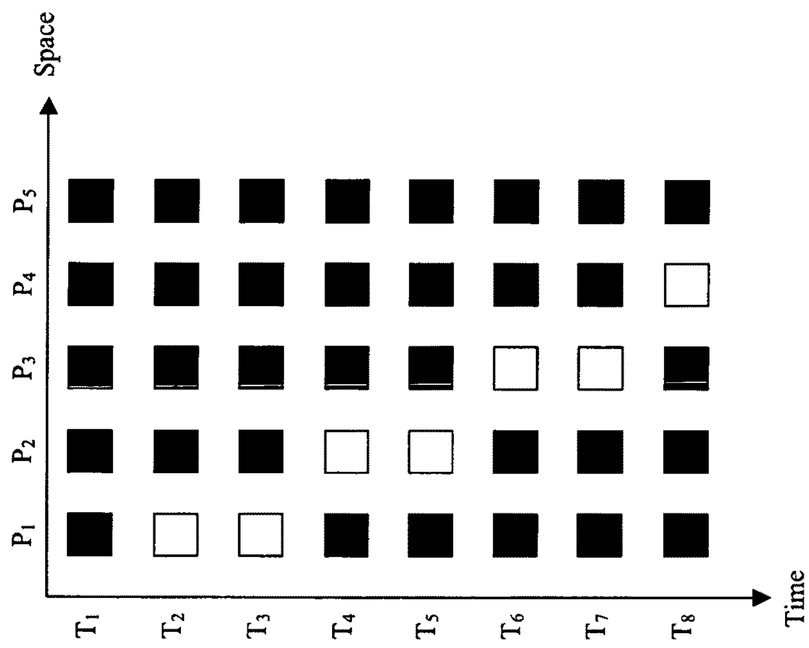

Similar considerations apply by taking into consideration the scenario provided in FIG. 8*a* (repeated in FIG. 10*a*).

In this case as well, as shown in FIG. 10*b*, all the pixels $P_1$-$P_5$ become black. As a consequence, the contribution of the slowly moving circulating particle of contrast agent is removed (even if it remains at the same pixel location for two consecutive instants).

More generally, the modified Min_IP algorithm may be defined by the following formula:

$$OP(x,y,k)=\mathrm{MIN}[IP(x,y,k), \ldots ,IP(x,y,k-n)] \text{ with } n>=1,$$

where n is the number of images specifying the filtering length. The filtering length n corresponds to a time window (given by the product of the filtering length n by the inverse of the sampling rate of the images), which defines the degree of temporal low-pass filtering applied by the modified Min_IP algorithm. Indeed, the modified Min_IP algorithm is able to remove any peak of the pixel values over time having a width smaller than the extent of the filtering window (while broader peaks remain partially visible). This improves the robustness of the method, thereby increasing the differentiability between immobilized contrast agent and circulating contrast agent.

The value of the filtering length n (and then of the filtering window) is tuned according to the opposed requirements of high accuracy and fast response of the analysis process. Particularly, higher values of the filtering length n allow removing circulating particles of contrast agent at a high concentration or circulating particles of contrast agent moving very slowly. However, this delays the instant at which any immobilized particle of contrast agent is detected (since the corresponding pixel becomes white only after the particle of contrast agent has remained at the same location for the extent of the corresponding filtering window); moreover, a pixel may remain black after turning black (even for a single instant) at intervals shorter than the length of the filtering window (for example, because of a noise in the images).

The filtering length n may be selected dynamically according to the specific application. Particularly, the filtering length n is set to low values (for example, n=1-5 corresponding to a filtering window of 0.1-0.5 s for a sampling rate of 10 images per second) when the contrast agent has a high flow rate (such as in arteries); conversely, the filtering length n is set to high values (for example, n=3-12 corresponding to a filtering window of 0.3-1.2 s for the same sampling rate of the images) when the contrast agent has a low flow rate (such as in capillaries).

Figure 11:
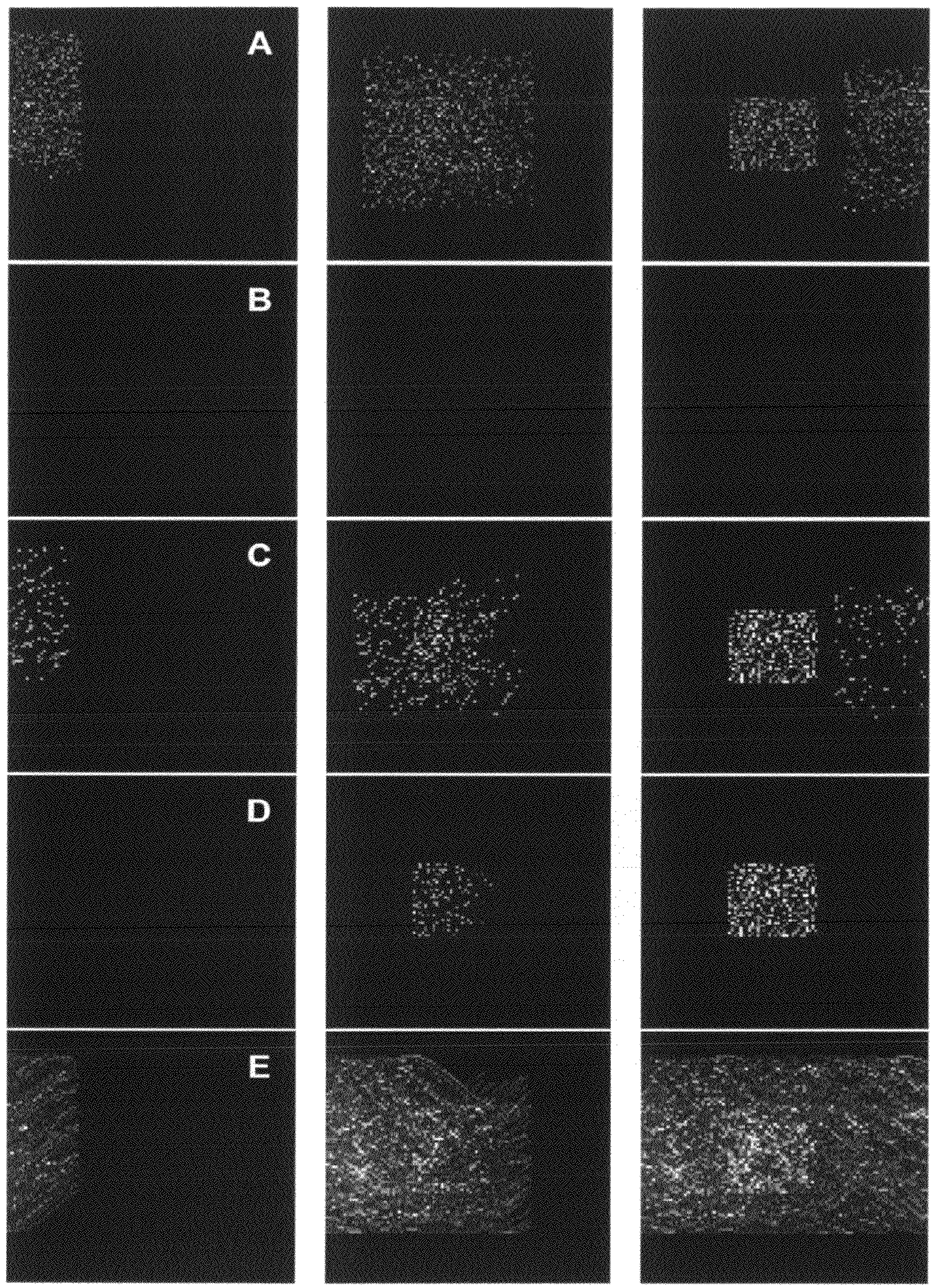
FIG. 11 shows the simulation of an exemplary application of the different algorithms.

The simulation of an exemplary application of the different algorithms described above is illustrated in FIG. 11. Particularly, the FIG. shows the results that are obtained on a synthetic dataset simulating different time instants of the passage of a volume of contrast agent (consisting of, for example, gas-filled microvesicles) over a target region (located in the center of the images). The left-most column illustrates the situation before the contrast agent has reached the target region (wash-in phase), the middle column illustrates the situation when the contrast agent overlaps the target region, and the right-most column illustrates the situation when the contrast agent has passed the target region (wash-out phase).

Row (A) represents the original sequence. As can bee seen, the immobilized contrast agent (in the target region) can be differentiated from the circulating contrast agent (and then detected) only after all the circulating particles of contrast agent have left the target region. In the case the contrast agent is administered through a bolus injection, this can take several minutes; for contrast agent administered as an infusion, which typically lasts for 10 minutes, the wash-out starts only after the infusion has been stopped.

Row (B) instead represents the result obtained with the application of the Min_IP algorithm. In this case, the images always remain black as was explained before; therefore, it is impossible to detect the immobilized contrast agent.

The result obtained with the modified Min_IP algorithm (using a filtering length n=1) is shown in row (C). In this case, the contribution of the circulating contrast agent is partially suppressed; however, the suppression is not complete and the immobilized particles of contrast agent are clearly visible and differentiable from the circulating particles of contrast agent only during the wash-out phase.

Row (D) represents the result obtained with the same modified Min_IP algorithm but setting a higher value of the filtering length (i.e., n=9). As can be seen, the contribution of the circulating contrast agent is now almost completely suppressed; therefore, it is possible to detect the immobilized particles of contrast agent as soon as they remain immobilized in the target region, without the need to wait for the wash-out phase of the contrast agent.

At the end, the result obtained with the Max_IP algorithm is shown in row (E). As discussed above, in this case the projection of the trajectory of each particle of contrast agent is nicely emphasized; however, those projected trajectories completely mask the immobilized particles of contrast agent (thereby making their detection impossible).

FIGS. 12*a*-12*d* now show an example of an in-vivo application of the above described modified Min_IP algorithm. For this purpose, a thrombus was induced in the abdominal artery of a guinea pig. This body-part was analyzed by means of an imaging probe of the linear array type (15L8) connected to a Sequoia ultrasound scanner (Siemens). The ultrasound scanner was operated in the CPS mode. The transmit frequency and mechanical index used were 10 MHz and 0.20, respectively. A bolus injection of contrast agent (consisting of fibrin-specific microbubbles) was administered at an initial instant t=0 min. The artery containing the thrombus was continuously scanned for a period of 10 min, including the wash-in and the wash-out of the contrast agent. The images so obtained were recorded on tape using a digital video recorder and processed off-line. In FIGS. 12*a*-12*d*, the original images are shown on the left-hand side. The modified Min_IP algorithm (with a filtering length n=9) was applied in a region of interest (ROI), which consisted of a rectangle including part of the artery with the thrombus; the results obtained were superimposed on the original images, so as to obtain the (processed) images shown on the right-hand side of the FIGS.

Figure 12A:
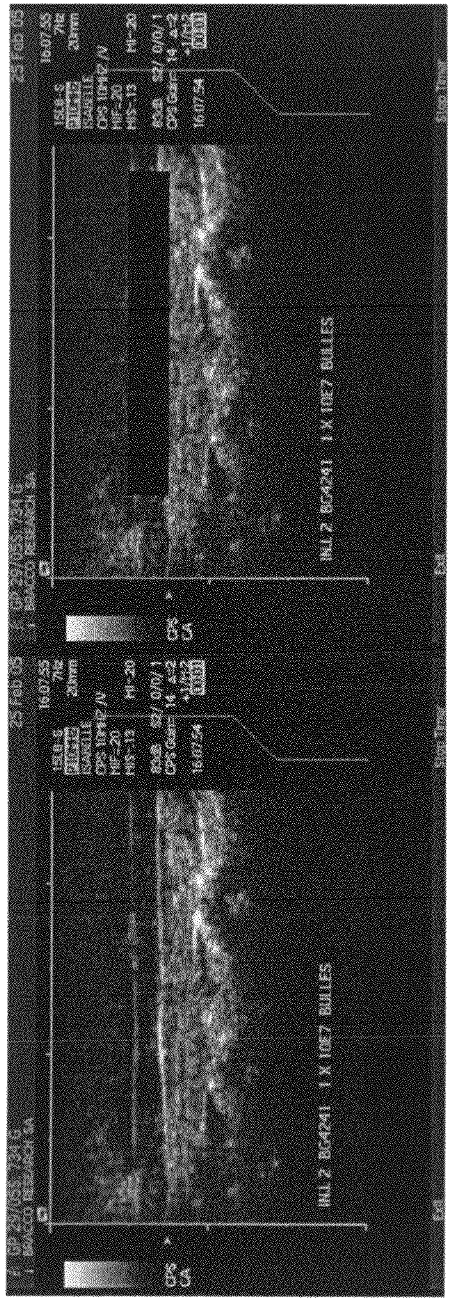
FIGS. 12*a*-12*d* show an example of in-vivo application of a solution according to an embodiment of the invention.

Particularly, FIG. 12*a* relates to the instant immediately after the injection of the contrast agent. As can be seen, the selected rectangle in the corresponding processed image is completely black, since the contrast agent has not yet reached the corresponding region of the body-part.

Figure 12B:
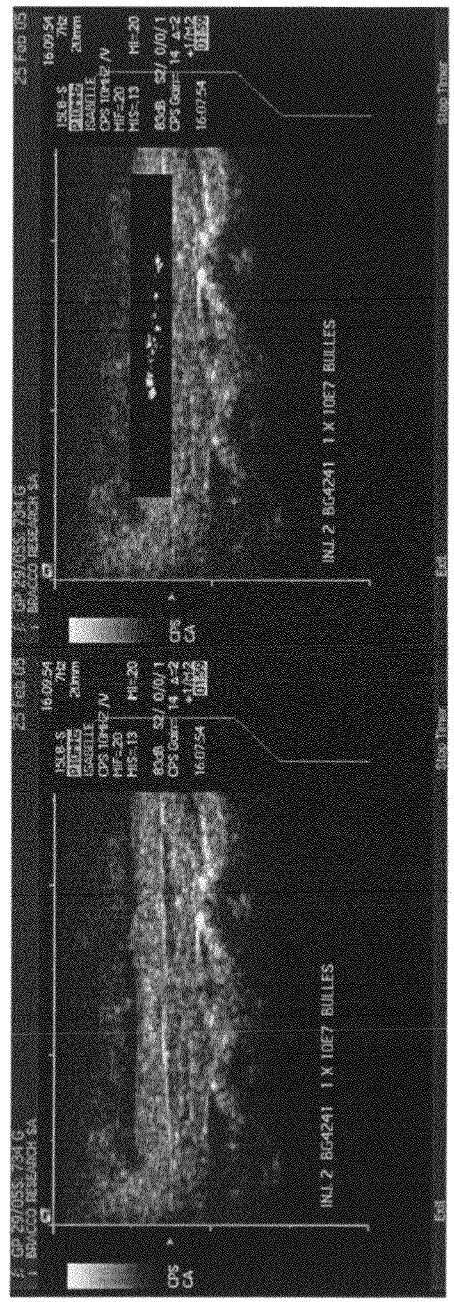

FIG. 12*b* depicts the situation 2 minutes after the injection of the contrast agent (during the wash-out phase). It is clear from the original image that the immobilized particles of contrast agent attached to the thrombus cannot be differentiated from the high concentration of circulating particles of contrast agent. In contrast, in the processed image the contribution of the circulating particles of contrast agent is nicely suppressed; in this way, the immobilized particles of contrast agent are clearly visible, perfectly outlining the thrombus.

Figure 12C:
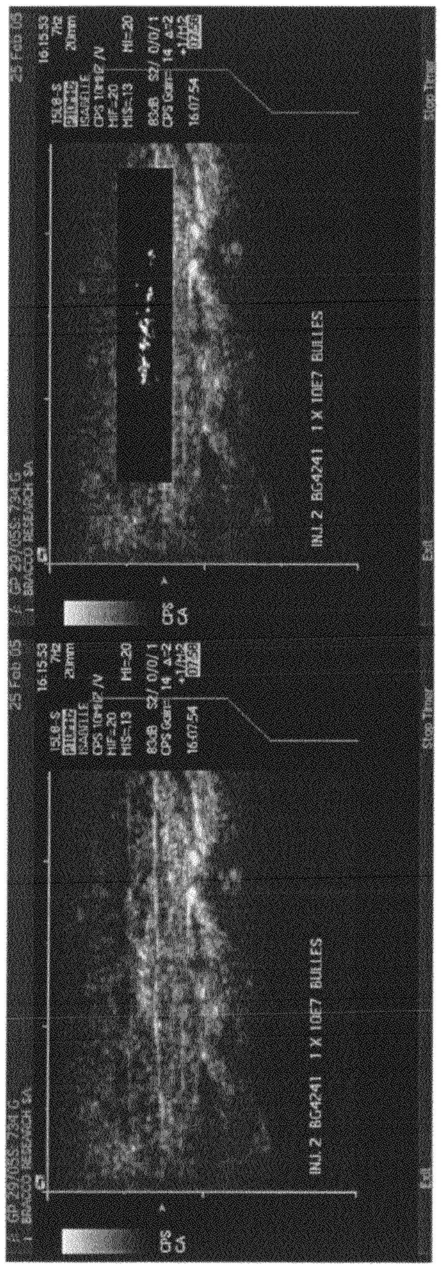
Figure 12D:
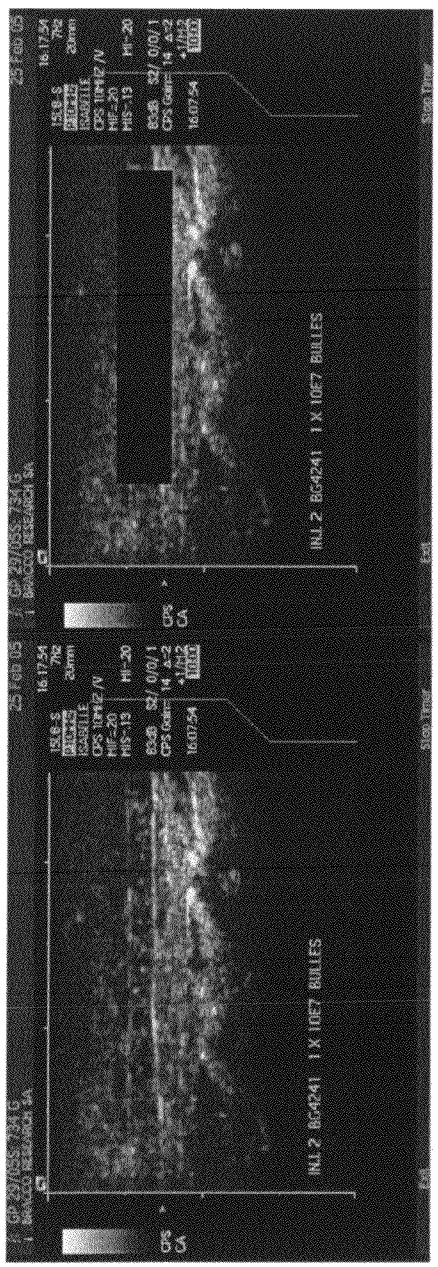

As shown in FIG. 12*c*, 8 minutes after the injection only a few particles of contrast agent are left in the circulation. This time, the immobilized particles of contrast agent attached to the thrombus can be seen in the original image too; however, the delineation of the thrombus is not as clear as shown in the processed image.

Finally, at the end of the experiment, ultrasound pulses with high mechanical index (a so-called flash) were used to destroy all the immobilized particles of contrast agent attached to the thrombus. The result so obtained in FIG. 12*d* confirms that the enhanced visualization of the thrombus was totally due to the attached particles of contrast agent.

Figure 13:
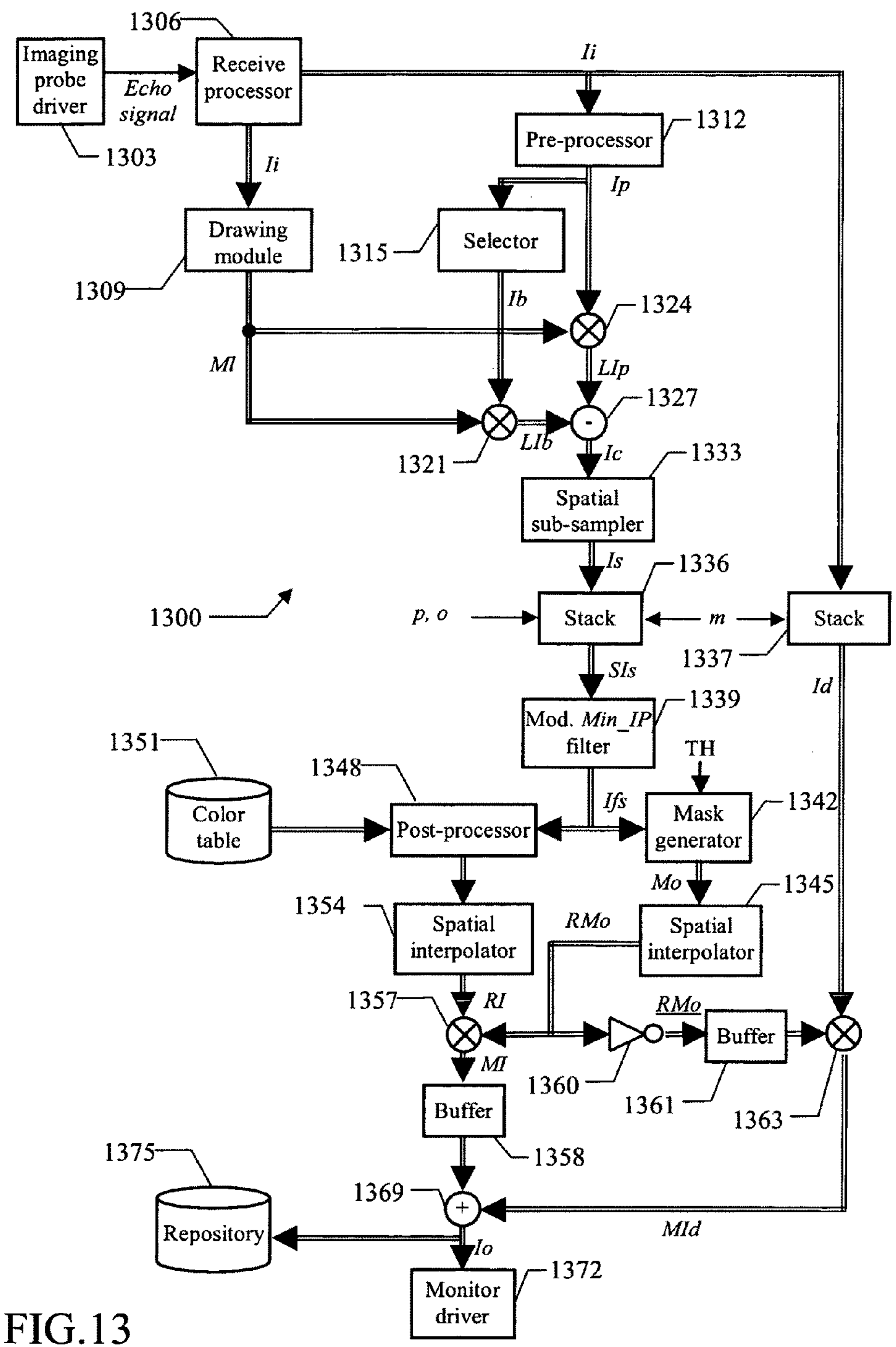
FIG. 13 depicts the main software and hardware components that can be used for practicing a solution according to an embodiment of the invention.

Moving now to FIG. 13, the main software and hardware components that can be used for practicing a solution according to an embodiment of the invention are denoted as a whole with the reference 1300. The information (programs and data) is typically stored on the hard disk and loaded (at least partially) into the working memory when the programs are running, together with an operating system and other application programs (not shown in the FIG.). The programs are initially installed onto the hard disk, for example, from CD-ROM.

Particularly, a driver 1303 controls the imaging probe (not shown in the FIG.); for example, the imaging probe driver 1303 includes a transmit beam former and pulsers for generating the ultrasound pulses to be applied to the body-part under analysis. The corresponding (analog RF) echo signal that is received from said body-part is supplied to a receive processor 1306. Typically, the receive processor 1306 pre-amplifies the analog RF echo signal and applies a preliminary time-gain compensation (TGC); the analog RF echo signal is then converted into digital values by an Analog-to-Digital Converter (ADC), and combined into a focused signal through a receive beam former. The digital signal so obtained may be processed through further digital algorithms and other linear or non-linear signal conditioners (such as a post-beam-forming TGC). Particularly, the receive processor 1306 applies a contrast-specific algorithm to suppress the contribution of the tissues (such as based on the above-mentioned HI, PI, PM or CPS techniques). The digital signal is then demodulated, log-compressed, and scan-converted into a video format. This process results in the recording of a sequence of (video) input images Ii. More specifically, each pixel value of the input images Ii is determined by the intensity of the acoustical response at the location in the body-part corresponding to said pixel. Optionally, the receive processor 1306 also includes a motion compensation module, carrying out a method for reducing the misalignment of the input images Ii with respect to a reference image (for example, due to motion of the patient, to his/her respiratory cycle or to the involuntary movement of the imaging probe); an example of motion compensation method that is well suited for this purpose is described in the co-pending International patent application PCT/EP2005/053871 filed on 5 Aug. 2005, the entire disclosure of which is herein incorporated by reference.

A drawing module 1309 is used to predefine a region-of-interest for the analysis process on the (possibly aligned) input images Ii. The operation generates a limitation mask Ml, which consists of a matrix of binary values with the same size as the input images Ii (i.e., M×N); all binary values inside the region of interest are assigned the logic value 1, whereas the binary values outside the region of interest are assigned the logic value 0.

A pre-processor 1312 is optionally used to convert the (video) input images into corresponding linearized input images, wherein each pixel value is directly proportional to the corresponding local concentration of the contrast agent; for example, this result can be achieved by applying an inverse log-compression and then squaring the value so obtained (for example, as described in WO-A-2004/110279, the entire disclosures of which is herein incorporated by reference). In any case, the pre-processor 1312 outputs a sequence of pre-processed input images Ip, which consists of the original (video) input images Ii or of the corresponding linearized input images (according to the user's choice).

A selector 1315 is used to extract and latch one of the pre-processed (video or linearized) input images Ip to be used as a background image (denoted with Ib); for example, the background image Ib is selected among the pre-processed input images Ip taken before the contrast agent has reached the body-part under analysis.

A multiplier operator 1321 receives the background image Ib (from the selector 1315) and the limitation mask Ml (from the drawing module 1309). The operator 1321 multiplies the background image Ib by the limitation mask Ml pixel-by-pixel, so as to generate a corresponding limited background image LIb (this operation needs to be done only once, but it can be repeated any time during the process). Another multiplier operator 1324 receives the pre-processed (video or linearized) input images Ip (from the pre-processor 1312) and the limitation mask Ml (from the drawing module 1309). The operator 1324 multiplies the pre-processed input images Ip by the limitation mask Ml pixel-by-pixel, so as to generate corresponding limited input images LIp. As a result, the limited background image LIb and the limited input images LIp only include the pixel values of the background image Ib and of the pre-processed input images Ip, respectively, that are inside the region of interest (defined by the limitation mask Ml), while the other pixel values are reset to 0.

A difference operator 1327 receives the limited background image LIb (from the multiplier 1321) and the limited input images LIp (from the multiplier 1324). The operator 1327 subtracts the limited background image LIb from the limited input images LIp pixel-by-pixel, so as to remove any residual clutter (for example, due the contribution of the tissues that has not been completely removed by the contrast-specific algorithm applied in the receive processor 1306). The operation generates a sequence of corrected images Ic, which are provided to a spatial sub-sampler 1333.

The module 1333 sub-samples the corrected images Ic according to a factor determined by the spatial resolution of the imaging probe along each dimension (equivalent to, for example, 2 to 6 pixels). The spatial sub-sampling may comprise low-pass filtering followed by sub-sampling according to a sub-sampling factor. The cutoff frequency of the low-pass filter may be chosen as the highest frequency component containing significant energy in one image selected from the corrected images Ic, for example, determined by Fourier analysis. The sub-sampling factor can then be determined, for example, as a value resulting in a spatial sampling frequency equal to twice the cutoff frequency. Each corrected image Ic is thus transformed into a (spatially sub-sampled) image Is.

The images Is are stored in succession into a stack 1336, which acts as a buffer memory for further processing according to the above-described algorithms. The stack 1336 provides storage for m images Is. The value of m is determined by the choice of the filtering depth n and a temporal sub-sampling parameter p (ranging from 0 to n−2), according to the relation $m=n(p+1)$. A set of n (temporally sub-sampled) images SIs is thus created and made available for further processing. In most practical situations, the parameter p is set to 0 so that m=n. The set of images SIs then consists of all the last n images Is stored in the stack 1336 (so that every image Is is considered). Conversely, when the sub-sampling parameter p is larger than 0, m images Is (m>n) are stored in the stack 1336, in order to make n images Is available for further processing. This temporal sub-sampling may be advantageously exploited when the ultrasound scanner works at ultrahigh sampling rates (for example, 100-500 images per second), in which case an analysis of every available image Is does not provide any useful benefit. The stack 1336 also receives an overlapping parameter o (ranging from 0 to m−1). Typically, the overlapping parameter o=m−1, so that the stack 1336 creates a new set of images SIs for each image Is. When the overlapping parameter o<m−1, the stack 1336 creates a new set of images SIs after m-o images Is have entered the stack 1336.

At the same time, the original (video) input images Ii provided by the receive processor 1306 are latched into another stack 1337, which consists of a first-in-first-out (FIFO) shift register, with a size equal to m (so as to store m input images Ii).

A filter 1339 receives the set of images SIs from the stack 1336. The filter 1339 calculates a filtered image Ifs by applying the above-described modified Min_IP algorithm on the set of images Sis (comprising n images Is).

The filtered image Ifs so obtained is then passed to a mask generator 1342, which also receives a predefined threshold value TH for the cell values (for example, ranging from 0 to 5% of their maximum allowable value). The mask generator 1342 creates a corresponding overlay mask Mo; the overlay mask Mo is obtained from the filtered image Ifs by assigning (to each cell) the logic value 1 if its value is strictly higher than the threshold value TH or the logic value 0 otherwise.

The overlay mask Mo is subsequently provided to a spatial-interpolator 1345. The spatial-interpolator 1345 restores the full-size of the overlay mask Mo corresponding to the size of the input images ii (i.e., M×N binary values); for this purpose, the value of each cell in the overlay mask Mo is replicated for the corresponding group of pixels. The operation generates a corresponding interpolated mask RMo.

At the same time, the filtered image Ifs is also provided to a post-processor 1348. The post-processor 1348 optionally converts the cell values of the filtered image Ifs into corresponding discrete values (for example, consisting of 64 or 128 levels that are uniformly distributed between the lowest value and the highest value of all the cells), by possibly applying a gain factor. Optionally, when the input images Ii are linearized by the pre-processor 1312, the post-processor 1348 may also apply a non-linear processing (such as a log-compression) so as to produce images with well-balanced contrast. The post-processor 1348 also accesses a color look-up table 1351. The color look-up table 1351 associates all the possible levels with the representation of corresponding colors (that may be brighter as the levels increase); for example, each color is defined by an index for accessing a location within a palette containing its actual specification. In this way, each cell in the filtered image Ifs is assigned the corresponding color representation.

The filtered image Ifs (either post-processed or as originally built) is provided to a spatial-interpolator 1354. The spatial-interpolator 1354 restores the full-size of the filtered image Ifs corresponding to the size of the input images Ii (i.e., M×N pixel values) by means of interpolation techniques (such as based on the nearest neighbor, bilinear, or bicubic technique). For this purpose, the value of each cell in the filtered image Ifs is replicated for the corresponding group of pixels (nearest neighbor interpolation method) and optionally filtered spatially (such as using a low-pass 2D or 3D spatial filter). The operation generates a corresponding interpolated image RI.

A multiplier operator 1357 receives the interpolated image RI (from the spatial interpolator 1354) and the interpolated mask RMo (from the spatial interpolator 1345). The operator 1357 multiplies the interpolated image RI by the interpolated mask RMo pixel-by-pixel, so as to obtain a masked image MI; as a result, the masked image MI only includes the pixel values of the corresponding interpolated image RI that are higher than the threshold value TH (while the other pixel values are reset to 0). The threshold value TH allows tuning the level of masking of the interpolated image RI; particularly, when the threshold value TH is set to 0, every pixel of the overlay mask Mo and of the interpolated overlay mask RMo is at the logic value 1, so that the masked image MI will be exactly the same as the interpolated image RI. The masked image MI is then latched into a single-image buffer 1358 (replacing its previous content). In this way, the masked image MI in the buffer 1358 is updated whenever a new filtered image Ifs is output by the filter 1339, while it remains unchanged otherwise (so as to maintain the masked image MI that was obtained from the filtered image Ifs last calculated).

The interpolated mask RMo is also supplied from the spatial interpolator 1345 to an inverter 1360, which generates a corresponding inverted interpolated mask RMo (by exchanging the logic values 0 and 1). The interpolated mask RMo is likewise latched into another single-image buffer 1361 (replacing its previous content), so as to be always synchronized with the masked image MI in the buffer 1358. The inverted interpolated mask RMo latched in the buffer 1361 is then passed to a multiplier operator 1363. The multiplier operator 1363 also receives a delayed image Id from the stack 1337. Every time the inverted interpolated mask RMo is latched into the buffer 1361, the corresponding delayed image Id exits from the stack 1337, thus allowing the operator 1363 to multiply its inputs, pixel-by-pixel, so as to obtain a masked delayed image MId; as a result, the masked delayed image MId only includes the pixel values of the delayed image Id that are not included in the corresponding masked image MI (while the other pixel values are reset to 0).

An adder operator 1369 receives the masked delayed image MId (from the multiplier 1363) and the masked image MI (latched in the buffer 1358). The operator 1369 adds the masked image MI and the masked delayed image MId pixel-by-pixel (correctly synchronized) so as to obtain an overlaid image Io. In this way, each pixel value of the delayed image Id is overridden by the corresponding pixel value of the masked image MI if and only if the latter has a significant value (i.e., higher than the threshold value TH).

The overlaid image Io is passed to a monitor driver 1372, which controls its visualization. At the same time, the overlaid image Io may also be added to a repository 1375. The same operations described above are reiterated for each new input image Ii that is recorded. Particularly, the new input image Ii is pushed into the stack 1337; this causes the shifting of the preceding input images Ii in the stack 1337, and the output of the oldest one. At the same time (after the possible linearization, the limitation to the desired region of interest, the subtraction of the background image Ib, and the spatial sub-sampling) the corresponding new corrected image Ic is added to the stack 1336. As a result, the overlaid images Io are displayed in succession on the monitor of the ultrasound scanner; it should be noted that each overlaid image Io is available with a delay (with respect to its acquisition time), which is defined by the time required to cross the whole stack 1337 (corresponding to the selected filtering window). Moreover, the sequence of overlaid images Io so obtained is also available in the repository 1375 for further analysis.

Embodiments described above facilitate the detection of the immobilized contrast agent; particularly, this allows discriminating the immobilized contrast agent from the circulating contrast agent (and from moving tissues as well). Therefore, the accuracy of any analysis of the obtained results is strongly increased.

More specifically, this technique makes it possible to spatially delineate the immobilized contrast agent in the region of interest of the body-part; at the same time, it allows quantifying the concentration of the immobilized contrast agent at each location with a relatively high degree of accuracy. For example, this facilitates the correct diagnosis of several pathologies that would otherwise be difficult to detect.

It should be noted that the detection of the immobilized contrast agent is now possible in real-time (while the images are displayed). Particularly, the immobilized particles of contrast agent are revealed as soon as they remain attached to the target; therefore, the results of the analysis may be available at an early time point after the administration of the contrast agent (without the need of waiting for its complete wash-out).

All of the above contributes to the successful development of new imaging techniques based on the use of targeted contrast agents.

The reading of the sequence of overlaid images Is further facilitated when they are displayed in color, as defined by the color representations assigned to the cells during the process of building the (interpolated) filtered images. In this case, each different color bears a quantitative meaning of its own; for example, this value can be read out from a color bar, which is displayed on the monitor close to the sequence of overlaid images.

Moreover, the overlay of the filtered images on the input images provides an enhanced visual perception of the immobilized contrast agent, which is now contextualized on the actual representation of the body-part under analysis. It should also be noted that the threshold value TH allows tuning the degree of the overlay according to contingent requirements. For example, an increase of the threshold value TH reduces the overlay, so as to limit the impact of the process on the (original) input images. Conversely, by setting the threshold value TH to 0 it is possible to superimpose the filtered images completely onto the input images in the region of interest.

Modifications

Naturally, in order to satisfy local and specific requirements, a person skilled in the art may apply to the solution described above many modifications and alterations. Particularly, although the present invention has been described with a certain degree of particularity with reference to embodiment(s) thereof, it should be understood that various omissions, substitutions and changes in the form and details as well as other embodiments are possible; moreover, it is expressly intended that specific elements and/or method steps described in connection with any disclosed embodiment, of the invention may be incorporated in any other embodiment as a general matter of design choice.

For example, similar considerations apply if the ultrasound scanner has a different structure or includes other units (such as with an imaging probe of the linear-, convex-, phased-, or matrix-array type). Alternatively, the proposed solution is applied in a medical imaging system that consists of an ultrasound scanner and a distinct computer (or any equivalent data processing system); in this case, the measured data is transferred from the ultrasound scanner to the computer for its processing (for example, through a removable disk, a memory key, or a network connection). In any case, the application to any other medical imaging application, such as based on Magnetic Resonance Imaging (MRI) or X-ray Computed Tomography (CT), is within the scope of the invention.

Likewise, an embodiment of the invention lends itself to be put into practice with equivalent contrast agents for whatever (biological) target; for example, in the above-mentioned alternative applications, the contrast agent may be specific for enhancing Magnetic Resonance imaging or X-ray Computed Tomography imaging.

In any case, nothing prevents the application of the proposed processing to the whole images (without selecting any region of interest).

As described above, an embodiment of the invention is implemented by calculating the minimum among the relevant pixel values (so as to facilitate removing the effects of overlapping speckle grains generated by the circulating particles of contrast agent). However, this is not to be intended as a limitation; indeed, alternative algorithms may be used to calculate values generically indicative of the lowest values in the relevant set (for example, based on weighted averages of the pixel values). More generally, an embodiment replaces the pixel values in the input images with filtered values that are representative of the lowest response (to the ultrasound pulses) of the corresponding pixel locations; therefore, in a system based on negative images (wherein the pixel values decrease with the intensity of the echo signal) this would mean calculating the maximum in the set.

Without departing from the principles of the invention, the filtering window (and then the filtering length) may also be defined in a different way. In any case, nothing prevents the use of a predefined filtering window (for example, set to a value providing acceptable performance in most standard situations).

Alternatively, the temporal sub-sampling of the input images may be performed according to any other criteria (or it may be omitted altogether).

Moreover, any other technique for acquiring the input images is within the scope of the present invention (for example, using Doppler-based algorithms).

It should be appreciated that the feature relating to the subtraction of the background image is not strictly necessary (and it may be omitted in some implementations of the invention).

Similar considerations apply if the input images are subsampled with a different technique (for example, according to a predefined sub-sampling factor); in any case, the application of the proposed solution at the pixel level (instead of at the level of groups of pixels defined by the above-mentioned spatial sub-sampling) is not excluded.

Likewise, it is also possible to omit compensating the motion of the input image (for example, when this motion is far slower than the flow of the contrast agent).

Alternatively, the spatial sub-sampling may be applied after filtering the images, instead of being applied before their storing into the corresponding stack.

It is also possible to leave the choice of overlaying the filtered images on the input images to the preference of a user. For example, the filtered images may be displayed alone without being overlaid on the input images or the pixel values of the input images within the region of interest may be set to zero in order to display the filtered images against a black background that may improve contrast. According to an alternative embodiment, the filtered images are overlaid on non contrast-specific images (such as fundamental B-mode images extracted from the contrast-specific images provided by the receive processor), the filtered images being nevertheless generated from images provided by a contrast-specific imaging mode. Moreover, although an embodiment of the present invention has been specifically designed for use in real-time, the application of a devised solution for analyzing the obtained results off-line is contemplated.

An embodiment can be extended by the implementation of two or more filters in parallel that apply the modified Min_IP algorithm with different filtering lengths. This would enable identifying particles of contrast agent with different flow rates at the same time (such as fast moving, slow moving and immobilized particles of contrast agent).

Similar considerations apply if the program (which may be used to implement the invention) is structured in a different way, or if additional modules or functions are provided; likewise, the memory structures may be of other types, or may be replaced with equivalent entities (not necessarily consisting of physical storage media). Moreover, an embodiment of the proposed solution lends itself to be implemented with an equivalent method (having similar or additional steps, even in a different order). In any case, the program may take any form suitable to be used by or in connection with any data processing system, such as external or resident software, firmware, or microcode (either in object code or in source code). Moreover, the program may be provided on any computer-usable medium; the medium may be any element suitable to contain, store, communicate, propagate, or transfer the program. Examples of such medium are fixed disks (where the program can be pre-loaded), removable disks, tapes, cards, wires, fibers, wireless connections, networks, broadcast waves, and the like; for example, the medium may be of the electronic, magnetic, optical, electromagnetic, infrared, or semiconductor type.

In any case, an embodiment according to the present invention lends itself to be carried out with a hardware structure (for example, integrated in a chip of semiconductor material), or with a combination of software and hardware.

The invention claimed is:

1. A system for facilitating detection of an immobilized contrast agent in medical imaging applications, the system including:

a receiving component configured to receive a sequence of a total number of input images obtained at corresponding acquisition instants by imaging a body-part of a patient subjected to an administration of a contrast agent capable of circulating within the patient and of being substantially immobilized on a biological target, each input image including a plurality of input values each one indicative of a response to an interrogation signal of a corresponding portion of the body-part possibly including said contrast agent, a reducing component configured to reduce a contribution of the circulating contrast agent within the body-part in at least one selected input image, wherein the reducing component includes a filtering component configured to create a filtered image for each selected input image, the filtered image being created from a set of multiple input images consisting of a number of input images lower than the total number, the set of multiple input images including the selected input image and at least one other input image the acquisition instant of which is at a predefined time distance from the acquisition instant of the selected input image by replacing a set of input values of the selected input image with a set of corresponding filtered values, each filtered value being representative of a lowest response of the corresponding portion of the body-part in the set of multiple input images; and a display component operable for displaying each filtered image for use in analyzing the body-part.

2. The system according to claim 1, wherein each input value increases with the response to the interrogation signal of the corresponding portion of the body-part, each filtered value consisting of a minimum among the corresponding input values in the set of multiple input images.

3. The system according to claim 1, wherein the set of multiple input images consists of the selected input image and at least one preceding input image in the sequence.

4. The system according to claim 3, wherein the at least one preceding input image consists of a plurality of preceding input images.

5. The system according to claim 3, further including:

a selecting component configured to select the number of preceding input images as a function of an estimated flow rate of the contrast agent in the body-part.

6. The system according to claim 1, further including a sub-sampling component configured for temporally sub-sampling the preceding input images.

7. The system according to claim 1, wherein the body-part includes a tissue, the receiving component including: a further reducing component configured to reduce a contribution of the tissue in the input images.

8. The system according to claim 1, wherein the filtering component includes:

a selecting component configured to select a background image in the sequence of input images, and a subtracting component configured to subtract the background image from the set of multiple input images.

9. The system according to claim 1, wherein the filtering component includes: a spatially-sub-sampling component configured for spatially sub-sampling the set of multiple input images according to an estimated resolution thereof.

10. The system according to claim 1, further including a selecting component configured to select a reference image in the sequence of input images and for compensating a motion of each input image with respect to the reference image.

11. The system according to claim 1, further including a linearizing component configured to linearize the set of multiple input images to make each input value thereof substantially proportional to a concentration of the contrast agent in the corresponding portion of the body-part.

12. The system according to claim 1 wherein the display component is further configured to display each filtered image substantially in real-time with the acquisition instant of the corresponding selected input image.

13. The system according to claim 1, wherein the filtering component includes:

a resetting component configured to reset each filtered value in the filtered image not reaching a threshold value, and a overlaying component configured to overlay the filtered image on the corresponding selected input image.

14. A method for improving the performance of a data processing system by facilitating detection of an immobilized contrast agent in medical imaging applications, the method including the steps of:

providing a sequence of a total number of input images obtained at corresponding acquisition instants by imaging a body-part of a patient subjected to an administration of a contrast agent capable of circulating within the patient and of being substantially immobilized on a biological target, each input image including a plurality of input values each one indicative of a response to an interrogation signal of a corresponding portion of the body-part possibly including said contrast agent, reducing a contribution of the circulating contrast agent within the body-part in at least one selected input image, wherein for each selected input image the step of reducing includes creating a corresponding filtered image by replacing a set of input values of the selected input image with a set of corresponding filtered values, the filtered image being created from a set of multiple input images consisting of a number of input images lower than the total number, the set of multiple input images including the selected input image and at least one other input image the acquisition instant of which is at a predefined time distance from the acquisition instant of the selected input image, each filtered value being representative of the lowest response of the corresponding portion of the body-part in the set of multiple input images, and displaying each filtered image for use in analyzing the body-part.

15. A non-transitory computer readable medium comprising a computer program for performing the method of claim 14 when the computer program is executed on a computer.

16. A computer program product including a non-transitory tangible computer-usable medium embodying a computer program, the computer program when executed on a data processing system causing the system to perform a method for facilitating the detection of an immobilized contrast agent in medical imaging applications, wherein the method includes the steps of:

providing a sequence of a total number of input images obtained at corresponding acquisition instants by imaging a body-part of a patient subjected to an administration of a contrast agent capable of circulating within the patient and of being substantially immobilized on a biological target, each input image including a plurality of input values each one indicative of a response to an interrogation signal of a corresponding portion of the body-part possibly including said contrast agent, reducing a contribution of the circulating contrast agent within the bodypart in at least one selected input image, wherein for each selected input image the step of reducing includes:

creating a corresponding filtered image by replacing a set of input values of the selected input image with a set of corresponding filtered values, the filtered image being created from a set of multiple input images consisting of a number of input images lower than the total number, the set of multiple input images including the selected input image and at least one other input image the acquisition instant of which is at a predefined time distance from the acquisition instant of the selected input image, each filtered value being representative of the lowest response of the corresponding portion of the body-part in the set of multiple input images, and displaying each filtered image for use in analyzing the body-part.

* * * * *